United States Patent
Brugarolas

(10) Patent No.: US 10,160,695 B2
(45) Date of Patent: Dec. 25, 2018

(54) SYNTHESIS OF META-SUBSTITUTED [$^{18}$F]-3-FLUORO-4-AMINOPYRIDINES BY DIRECT RADIOFLUORINATION OF PYRIDINE N-OXIDES

(71) Applicant: The University of Chicago, Chicago, IL (US)

(72) Inventor: Pedro Brugarolas, Chicago, IL (US)

(73) Assignee: The University of Chicago, Chicago, IL (US)

(*) Notice: Subject to any disclaimer, the term of this patent is extended or adjusted under 35 U.S.C. 154(b) by 0 days.

(21) Appl. No.: 15/497,747

(22) Filed: Apr. 26, 2017

(65) Prior Publication Data

US 2017/0355648 A1 Dec. 14, 2017

Related U.S. Application Data

(60) Provisional application No. 62/327,664, filed on Apr. 26, 2016.

(51) Int. Cl.
*C07D 213/73* (2006.01)
*C07B 59/00* (2006.01)
*C07D 471/04* (2006.01)

(52) U.S. Cl.
CPC .......... *C07B 59/002* (2013.01); *C07D 213/73* (2013.01); *C07D 471/04* (2013.01); *C07B 2200/05* (2013.01)

(58) Field of Classification Search
CPC . C07B 59/002; C07B 2200/05; C07D 213/71; C07D 471/04; C07D 213/73
See application file for complete search history.

(56) References Cited

U.S. PATENT DOCUMENTS

| | | |
|---|---|---|
| 9,617,215 B2 | 4/2017 | Brugarolas et al. |
| 2014/0004044 A1 | 1/2014 | Brugarolas et al. |
| 2017/0174629 A1 | 6/2017 | Brugarolas et al. |

OTHER PUBLICATIONS

Abrahim, J Labelled Compd, Radiopharm, vol. 49(4), 345-356, 2006. (Year: 2006).*
Abrahim et al., "Synthesis of fluorine-18-labelled 5- and 6-fluoro-2-pyridinamine," *Journal of Labelled Compounds and Radiopharmaceuticals*, 2006; 49: 345-356.
Beer et al., "Comparison of two synthetic methods to obtain [18F] N-(2-aminoethyl)-5-fluoropyridine-2-carboxamide, a potential MAO-B imaging tracer for PET," *Journal of Labelled Compounds and Radiopharmaceuticals*, 1995; 36: 933-945.
Blom et al., "[$^{18}$F]/$^{19}$F exchange in fluorine containing compounds for potential use in 18F-labelling strategies," *Journal of Labelled Compounds and Radiopharmaceuticals*, 2009; 52: 504-511.
Brugarolas et al. *Journal of Nuclear Medicine*, 2015; 56: 493.
Brugarolas et al., *J Nucl Med Meeting Abstracts*, 2014; 55: 1124.
Carroll et al., "Diaryliodonium salts: a solution to 3-[$^{18}$F]fluoropyridine," *Journal of Labelled Compounds and Radiopharmaceuticals*, 2007; 50: 452-454.
Chun et al., "Selective syntheses of no-carrier-added 2- and 3-[$^{18}$F]fluorohalopyridines through the radiofluorination of halopyridinyl(4'-methoxyphenyl)iodonium tosylates," *Chem Commun (Camb)*, 2012; 48: 9921-9923.
Chun et al., "No-carrier-added [$^{18}$F]fluoroarenes from the radiofluorination of diaryl sulfoxides," *Chem Commun (Camb)*, 2013; 49: 2151-2153.
Johnson, "Nucleophilic displacements in substituted pyridine N-oxides. Part I. Kinetics of the reactions between sodium ethoxide and 2- and 4-bromo-, 4-chloro-, 2-, 3-, and 4-nitro-, 4-chloro-3,5-dimethyl-, and 3,5-dimethyl-4-nitro-pyridine 1-oxide in anhydrous ethanol," *Journal of the Chemical Society B: Physical Organic*, 1966; 1058-1061.
Karramkam et al., "2-, 3- and 4-[$^{18}$F]Fluoropyridine by no-carrier-added nucleophilic aromatic substitution with K[$^{18}$F]F-K$_{222}$—a comparative study," *Journal of Labelled Compounds and Radiopharmaceuticals*, 2003; 46: 979-992.
Liu et al., "Development of $^{18}$F-Labeled Picolinamide Probes for PET Imaging of Malignant Melanoma," *Journal of Medicinal Chemistry*, 2013; 56: 895-901.
Liu et al., "Preclinical Evaluation of a High-Affinity $^{18}$F-Trifluoroborate Octreotate Derivative for Somatostatin Receptor Imaging," *Journal of Nuclear Medicine*, 2014; 55: 1499-1505.
Liu et al. "$^{18}$F-Trifluoroborate Derivatives of [Des-Arg$^{10}$]Kallidin for Imaging Bradykinin B1 Receptor Expression with Positron Emission Tomography," *Mol. Pharm.* 2015; 12: 974-982.
Preshlock et al., "$^{18}$F-Labeling of Arenes and Heteroarenes for Applications in Positron Emission Tomography," *Chemical Reviews*, 2016; 116:719-766.
Rotstein et al., "Spirocyclic hypervalent iodine(III)-mediated radiofluorination of non-activated and hindered aromatics," *Nature Communications*, 2014; 5: 4365.
Tredwell and Grouverneur, "$^{18}$F Labeling of Arenes," *Angew Chem Int Ed Engl*, 2012; 51(46): 11426-11437.

* cited by examiner

*Primary Examiner* — D Margaret M Seaman
(74) *Attorney, Agent, or Firm* — Norton Rose Fulbright US LLP

(57) ABSTRACT

Disclosed herein are methods for the fluorination aromatic N-heterocyclic N-oxides that comprise at least one leaving group. The N-oxides may be reduced to the fluorinated aromatic N-heterocyclic amine analogs. This novel fluorination approach may be successfully applied for synthesizing aromatic N-heterocyclic compounds labeled with $^{18}$F.

18 Claims, 26 Drawing Sheets

SYNTHESIS OF META-SUBSTITUTED [$^{18}$F]-3-FLUORO-4-AMINOPYRIDINES BY DIRECT RADIOFLUORINATION OF PYRIDINE N-OXIDES

CROSS-REFERENCE TO RELATED APPLICATIONS

This application claims priority to U.S. Provisional Patent Application Ser. No. 62/327,664, filed on Apr. 26, 2016, which is hereby incorporated by reference in its entirety

BACKGROUND OF THE INVENTION

1. Field of the Invention

This invention relates to the fields of radiochemistry, synthetic organic chemistry, and radiopharmaceuticals.

2. Description of the Related Art

Due to their electron-rich aromatic structure, nucleophilic (radio)fluorination of pyridines is challenging, especially at the meta position.

Few methods exist to produce 3- or 5-fluoro-substituted pyridines compatible with the constraints of $^{18}$F radiochemistry, which include the use of fluoride ions as the fluorine source and short reaction times[1]. Customary methods for the synthesis of 2- and 4-fluoropyridines such as substitution of halides, nitro, trimethyl ammonium salts[2] or sulfonium salts[3], work in very low yield for the 3- and 5-positions. Furthermore, these methods are limited to pyridines containing secondary strong electron withdrawing groups such as nitrile or carboxamide[4-6]. Pyridines that do not contain secondary electron withdrawing groups are amenable to fluorination through recently-developed methods such as the use of iodonium salts[7,8] and iodonium ylides[9]. However, these methods often require precursors that are difficult to prepare.

Given the limited number of reactions yielding 3- and 5-fluoropyridines, there is a great need to develop new methods that are fast, react in high yield, and use readily available precursors.

SUMMARY OF THE INVENTION

Disclosed herein are methods for the synthesis of fluorinated aromatic, N-heterocyclic compounds. In some embodiments, the method entails reacting an aromatic N-heterocyclic N-oxide compound with a fluoride source to give a fluorinated aromatic N-heterocyclic N-oxide compound. In further embodiments, the fluorinated aromatic N-heterocyclic N-oxide compound may be further reduced to give a fluorinated aromatic N-heterocyclic compound. The methods disclosed herein may be employed for a number of fluorinated aromatic, N-heterocyclic compounds, as well as their N-oxide derivatives.

In some aspects, methods for synthesizing fluorinated aromatic N-heterocyclic compounds are presented. The methods entail reacting an aromatic N-heterocyclic N-oxide compound comprising a leaving group with a fluoride source to give a fluorinated aromatic N-heterocyclic N-oxide compound. In some embodiments, a method for using the fluorinated aromatic N-heterocyclic N-oxide compound are presented. Some embodiments are directed towards the use of a fluorinated aromatic N-heterocyclic N-oxide compound manufactured by a method comprising reacting an aromatic N-heterocyclic N-oxide compound with a fluoride source, wherein the aromatic Nheterocyclic N-oxide compound comprises a leaving group. The leaving group may be ortho-, meta-, or para- to the N-oxide. In some aspects, the leaving group is a halide, nitro, protonated ammonium, protonated alkylammonium, trialkylammonium, mesylate, tosylate, phenoxide, carboxylate, thiolate, or diazonium group.

In some aspects, the fluoride source is a nucleophilic fluoride source. The fluoride source may comprise non-naturally-occurring isotope of fluorine. In some embodiments, the non-naturally-occurring isotope is $^{18}$F. The fluorinated aromatic N-heterocyclic N-oxide compound may be reduced to give a fluorinated aromatic N-heterocyclic compound. In some embodiments, the nucleophilic fluoride source is selected from the group consisting of tetrabutylammonium fluoride (TBAF), tetramethylammonium fluoride (TMAF), (diethylamino)sulfur trifluoride (DAST), bis(2-methoxyethyl)aminosulfur trifluoride (deoxofluor), 4-morpholinosulfur trifluoride (MOST), CsF, NaF, KF, and KF-kryptofix.

In some embodiments, the fluorinated aromatic N-heterocyclic N-oxide compound may be reduced with a reducing composition to give a fluorinated N-heterocyclic compound. In some embodiments, a method for using a fluorinated N-heterocyclic compound is presented. Some embodiments are directed towards using a fluorinated aromatic N-heterocyclic compound manufactured by a method comprising reacting an aromatic N-heterocyclic N-oxide compound with a fluoride source; wherein the aromatic N-heterocyclic N-oxide compound comprises a leaving group, and reducing the N-oxide group of the aromatic N-heterocyclic N-oxide compound with a reducing composition to give a fluorinated aromatic N-heterocyclic compound. The reducing composition may be any reducing composition known to those in the art for reducing N-oxides to amines. In some embodiments, the reducing composition comprises hydrogen and a transition metal absorbed onto a solid support, a boron reagent, an aluminum reagent, a tin reagent, or a silane. The transition metal may be palladium, platinum, nickel, rhodium, or others. The solid support may be carbon, alumina, calcium carbonate, silica, or other solid supports known in the art. The boron reagent may be sodium borohydride, sodium cyanoborohydride, zinc borohydrode, a tetraorganylammonium tetrahydroborate, lithium triethylborohydride, lithium tri-sec-butyl borohydride, L-selectride, sodium triacetoxyborohydride, sulfurated sodium borohydride, or other reducing boron reagents. The aluminum reagent may be aluminum hydride, lithium aluminum hydride, lithium tri-tert-butoxy aluminum hydride, DIBAL-H, sodium bis(2-methoxyethoxy)aluminumhydride, or other aluminum reducing reagents. The tin reagent may be tributyltin hydride, or a different reducing tin reagent known to those of skill in the art. The silane reagent may be an alkylsilane, an alkylsiloxane, a phenylsilane, or a halosilane.

The aromatic N-heterocyclic N-oxide compound comprising a leaving group may be substituted or unsubstituted. In the context of the methods described herein, an unsubstituted aromatic N-heterocyclic N-oxide compound comprising a leaving group refers to an aromatic N-heterocyclic N-oxide compound where one of the aromatic carbon atoms is bound to a leaving group, and the other aromatic carbon atoms are bound to hydrogen atoms. A substituted aromatic N-heterocyclic N-oxide compound comprising a leaving group is a compound that includes a leaving group bound to one of the aromatic carbon atoms and at least one non-hydrogen group bound to a different aromatic carbon atom.

In some aspects, a method for synthesizing a fluoropyridine, or substituted derivative thereof, comprises reacting a pyridine N-oxide comprising a leaving group with a fluoride source to give an intermediate fluoropyridine N-oxide, and reducing the intermediate with a reducing composition to give the fluoropyridine. In some embodiments, a method for using the fluoropyridine is presented. Further embodiments are directed towards using a fluoropyridine compound manufactured by a method comprising reacting a pyridine N-oxide compound comprising a leaving group with a fluoride source to give an intermediate fluoropyridine N-oxide and reducing the intermediate composition to give the fluoropyridine compound. Some aspects are directed towards fluorinating a substituted halopyridine compound. In some aspects, the substituted halopyridine compound is a halonitropyridine. In further aspects, the substituted halopyridine compound is a 3-halo-4-nitropyridine N-oxide. The reducing composition may be any reducing composition known to those in the art for reducing N-oxides to amines. In some embodiments, the reducing composition comprises hydrogen and a transition metal absorbed onto a solid support, a boron reagent, an aluminum reagent, a tin reagent, or a silane. The transition metal may be palladium, platinum, nickel, rhodium, or others. The solid support may be carbon, alumina, calcium carbonate, silica, or other solid supports known in the art. The boron reagent may be sodium borohydride, sodium cyanoborohydride, zinc borohydrode, a tetraorganylammonium tetrahydroborate, lithium triethylborohydride, lithium tri-sec-butyl borohydride, L-selectride, sodium triacetoxyborohydride, sulfurated sodium borohydride, or other reducing boron reagents. The aluminum reagent may be aluminum hydride, lithium aluminum hydride, lithium tri-tert-butoxy aluminum hydride, DIBAL-H, sodium bis(2-methoxyethoxy)aluminumhydride, or other aluminum reducing reagents. The tin reagent may be tributyltin hydride, or a different reducing tin reagent known to those of skill in the art. The silane reagent may be an alkylsilane, an alkylsiloxane, a phenylsilane, or a halosilane.

In some aspects, a method for synthesizing a 3-fluoropyridine, or substituted derivative thereof, comprises reacting a 3-halopyridine N-oxide with a fluoride source to give an intermediate 3-fluoropyridine N-oxide, and reducing the intermediate with a reducing composition to give the 3-fluoropyridine. Some aspects are directed towards fluorinating a substituted halopyridine compound. In some aspects, the substituted halopyridine compound is a halonitropyridine. In further aspects, the substituted halopyridine compound is a 3-halo-4-nitropyridine N-oxide. The halogen may be a fluorine, chlorine, bromine, or an iodine. In the case where the halogen is a fluorine atom, fluoride exchange is observed. This fluoride exchange may be used to produce fluoride tracers by $^{19}F/^{18}F$ exchange.

In some aspects, a radiofluoride or non-naturally-occurring isotope of fluoride is employed as the fluoride source. Employing a radiofluoride or non-naturally-occurring isotope of fluoride provides a method for the synthesis of radiolabeled fluoropyridine compounds.

The term "coupled" is defined as connected, although not necessarily directly, and not necessarily mechanically.

The terms "a" and "an" are defined as one or more unless this disclosure explicitly requires otherwise.

The term "substantially" is defined as being largely but not necessarily wholly what is specified (and include wholly what is specified) as understood by one of ordinary skill in the art.

In any disclosed embodiment, the term "substantially" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a composition that "comprises," "has," "includes" or "contains" one or more elements possesses those one or more elements, but is not limited to possessing only those one or more elements. Likewise, an element of a system or composition that "comprises," "has," "includes" or "contains" one or more features possesses those one or more features, but is not limited to possessing only those one or more features.

Furthermore, a structure or composition that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the disclosed container assemblies and compositions can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

FIG. 1A Nucleophilic aromatic substitution of 3-bromo-4-(boc-amino)pyridine with tetrabutyl ammonium fluoride in DMSO at 125° C. followed by acid deprotection. Fluorination did not proceed under the experimental conditions. FIG. 1B Nucleophilic aromatic substitution of 3-bromo-4-nitropyridine and 3-iodo-4-nitropyridine with tetrabutyl ammonium fluoride in DMSO at 125° C. followed by reduction. The products formed were 3-bromo-4-fluoropyridine or 3-iodo-4-fluoropyridine instead of the desired products. FIG. 1C Nucleophilic aromatic substitution of 3-bromo-4-nitropyridine N-oxide with tetrabutyl ammonium fluoride in DMSO at 125° C. followed by reduction. Fluorination produced 3-fluoro-4-nitropyridine N-oxide (9) in 37% yield. Hydrogenation of 9 produced 3-fluoro-4-aminopyridine (10) in quantitative yield.

FIG. 2A Fluorination of 3-bromopyridine with tetrabutyl ammonium fluoride in DMSO at 120° C. for 12 hours did not produce the fluoride-substituted product. Fluorination of 3-bromopyridine N-oxide with tetrabutyl ammonium fluoride in DMSO at 120° C. produced the desired product after only 30 minutes of reaction time. FIG. 2B $^-$F fluorination of 3-bromo-4-nitropyridine N-oxide with tetrabutyl ammonium fluoride in DMSO at 25° C. for 15 minutes to produce the $^{18}$F fluorinated product 9. FIG. 2C Reduction of the nitro group with H$_2$ Pd/C produced the desired $^{18}$F 3-fluoro-4-aminopyridine 10.

FIG. 3A Co-injection of crude mixture from depicted reaction and reference standard. Unreacted [$^{18}$F]-TBAF, reaction product (9) and precursor (8) elute at 2.3, 9.65 and 18.25 min, respectively. FIG. 3B Injection of reaction crude of $^{19}$F/$^{18}$F reaction, unreacted [$^{18}$F]-TBAF and product elute at 2.3 and 5.3 min, respectively. FIG. 3C Co-injection of crude from depicted reaction and reference standard. Reaction product (10) elutes at 7.05 min, starting material (9) (minor peak) elutes at 5.80 min.

FIG. 4A UV HPLC traces at 254 nm and 313 nm. 3-bromo-4-nitropyridine (3) elutes at 10.85 min, and absorbs at 254 and 313 nm. 3-bromo-4-fluoropyridine (6) elutes at 11.88 min, and absorbs at 254 nm only. FIG. 4B $^1$H NMR. FIG. 4C $^{13}$C NMR. FIG. 4D $^{19}$F NMR.

FIG. 5A UV HPLC traces at 254 nm and 313 nm. 3-iodo-4-nitropyridine (4) elutes at 10.98 min, and absorbs at 254 and 313 nm. 3-iodo-4-fluoropyridine (7) elutes at 13.38 min, and absorbs at 254 nm only. FIG. 5B $^1$H NMR. FIG. 5C 19F NMR.

FIG. 6A UV HPLC traces at 254 nm and 313 nm. 3-bromo-4-nitropyridine N-oxide (8) elutes at 11.83 min, and absorbs at 254 and 313 nm. 3-fluoro-4-nitropyridine N-oxide (9) elutes at 7.95 min, and absorbs only at 254 and 313 nm. FIG. 6B $^1$H NMR. FIG. 6C $^{13}$C NMR. FIG. 6D $^{19}$F NMR.

FIG. 7A UV HPLC traces of desired product (top), starting bromide (middle), and reaction mixture (bottom). FIG. 7B $^1$H NMR. FIG. 7C $^{19}$F NMR.

FIG. 8A UV HPLC traces of product (top), starting material (middle), and reaction mixture (bottom). 8B $^1$H NMR. FIG. 8C $^{19}$F NMR.

FIG. 9A HPLC traces before hydrogenation. FIG. 9B HPLC trace after hydrogenation.

DETAILED DESCRIPTION

Figure 1A:
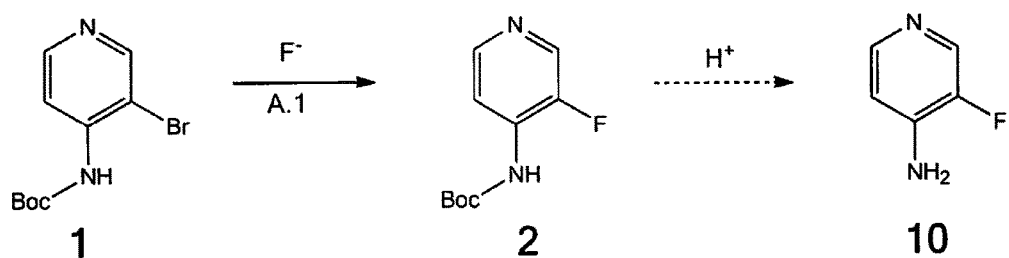
FIGS. 1A-1C. Fluorination strategies for 3-fluoro-4-aminopyridine.

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O) CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The term "aryl" or "aromatic" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl) phenyl, —C$_6$H$_4$CH$_2$CH$_3$, —C$_6$H$_4$CH$_2$CH$_2$CH$_3$, —C$_6$H$_4$CH (CH$_3$)$_2$, —C$_6$H$_4$CH(CH$_2$)$_2$, —C$_6$H$_3$(CH$_3$)CH$_2$CH$_3$, —C$_6$H$_4$CH=CH$_2$, —C$_6$H$_4$CH=CHCH$_3$, —C$_6$H$_4$C≡CH, —C$_6$H$_4$C≡CCH$_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, quinolyl, indolyl, and imidazoyl. In certain embodiments, heteroatom-substituted aryl groups are contemplated. In certain embodiments, heteroatom-unsubstituted aryl groups are contemplate. In certain embodiments, an aryl group may be mono-, di-, tri-, tetra- or penta-substituted with one or more heteroatom-containing substitutents.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted $C_n$-alkylamino, and heteroatom-substituted $C_n$-alkylamino. The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —$NHCH_3$, —$NHCH_2CH_3$, —$NHCH_2CH_2CH_3$, —$NHCH(CH_3)_2$, —$NHCH(CH_2)_2$, —$NHCH_2CH_2CH_2CH_3$, —$NHCH(CH_3)CH_2CH_3$, —$NHCH_2CH(CH_3)_2$, —$NHC(CH_3)_3$, —$N(CH_3)_2$, —$N(CH_3)CH_2CH_3$, —$N(CH_2CH_3)_2$, N-pyrrolidinyl, and N-piperidinyl.

The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "alkylsilyl" includes straight-chain alkylsilyl, branched-chain alkylsilyl, cycloalkylsilyl, cyclic alkylsilyl, heteroatom-unsubstituted alkylsilyl, heteroatom-substituted alkylsilyl, heteroatom-unsubstituted $C_n$-alkylsilyl, and heteroatom-substituted $C_n$-alkylsilyl. The term "heteroatom-unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted $C_1$-$C_{10}$-alkylsilyl has 1 to 10 carbon atoms. An alkylsilyl group includes dialkylamino groups. The groups, —$Si(CH_3)_3$ and —$Si(CH_3)_2C(CH_3)_3$, are non-limiting examples of heteroatom-unsubstituted alkylsilyl groups. The term "heteroatom-substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted $C_1$-$C_{10}$-alkylsilyl has 1 to 10 carbon atoms.

The present disclosure provides a method for synthesizing fluorinated aromatic N-heterocyclic compounds. In particular embodiments, the present disclosure provides a novel method for the synthesis of meta-substituted $^{18}$F 3-fluoro-4-aminopyridines by direct radiofluorination of pyridine N-oxides. 3-fluoro-4-aminopyridine is a fluorine-containing derivative of 4-aminopyridine, a clinically-approved drug for multiple sclerosis that binds to potassium channels in the central nervous system, currently under investigation for imaging demyelination[10-12]. The use of pyridine N-oxides for the preparation of fluoropyridines is unprecedented in the chemical literature and provides a novel approach for the synthesis of these important structures in pharmaceuticals and radiopharmaceuticals.

Derivatives of compounds of the present invention are also contemplated. In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S— or the R-configuration, as defined by the IUPAC 1974 Recommendations. Compounds may be of the D- or L-form, for example. It is well known in the art how to prepare and isolate such optically active forms. For example, mixtures of stereoisomers may be separated by standard techniques including, but not limited to, resolution of racemic form, normal, reverse-phase, and chiral chromatography, preferential salt formation, recrystallization, and the like, or by chiral synthesis either from chiral starting materials or by deliberate synthesis of target chiral centers.

Figure 1B:
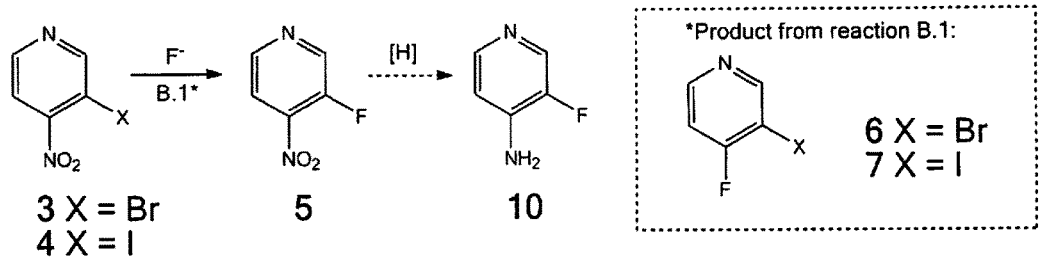
Figure 1C:
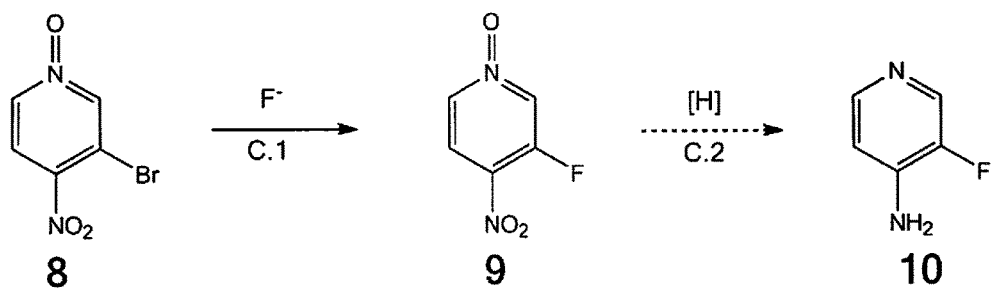

For the synthesis of [$^{18}$F]-3-fluoro-4-aminopyridine, three possible routes from commercially available reagents were considered (FIG. 1). The first route A.1 entailed fluorination of Boc-protected 3-bromo-4aminopyridine (1) followed by acid deprotection. Treatment of 1 with tetrabutylammonium fluoride (TBAF) did not produce the desired product even after several hours at high temperature.

Figure 3A:
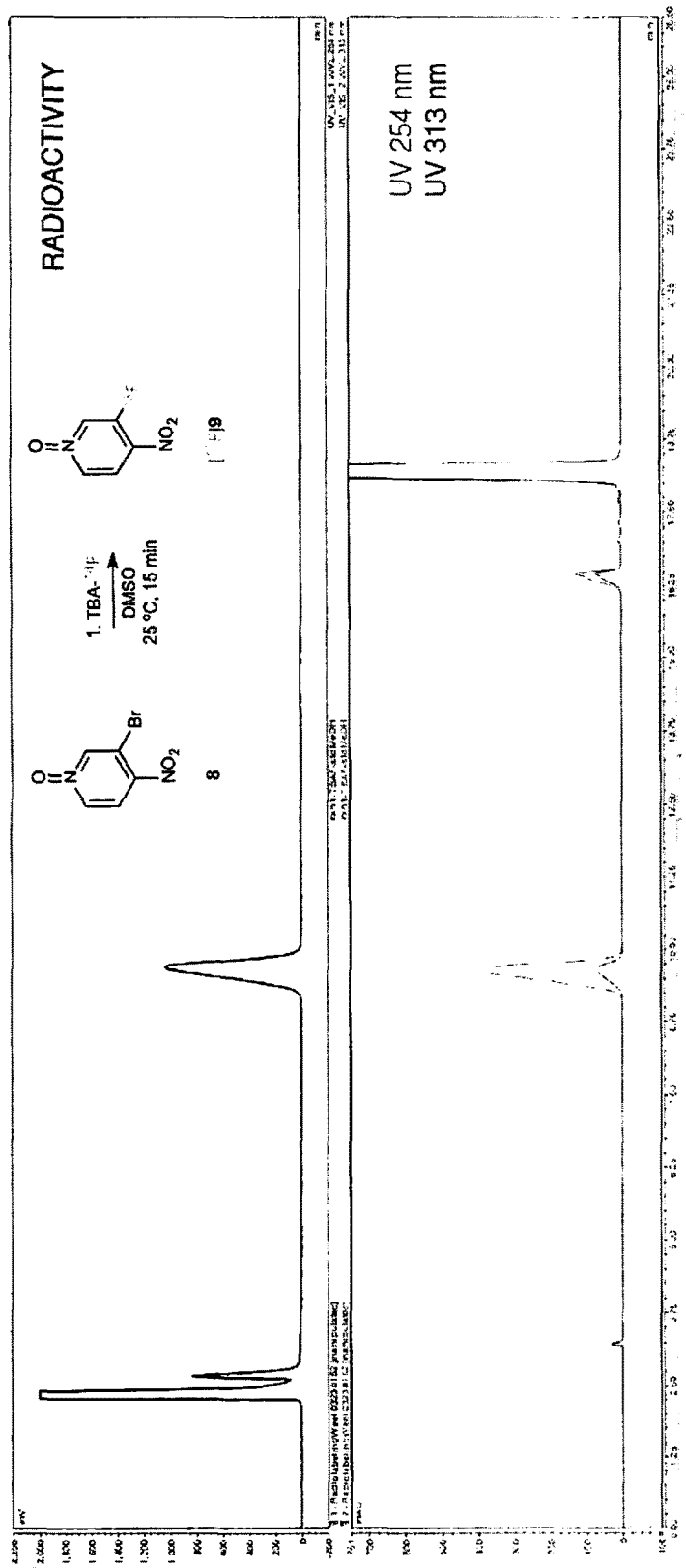
FIGS. 3A-3C Radioactive and UV HPLC traces.
Figure 3B:
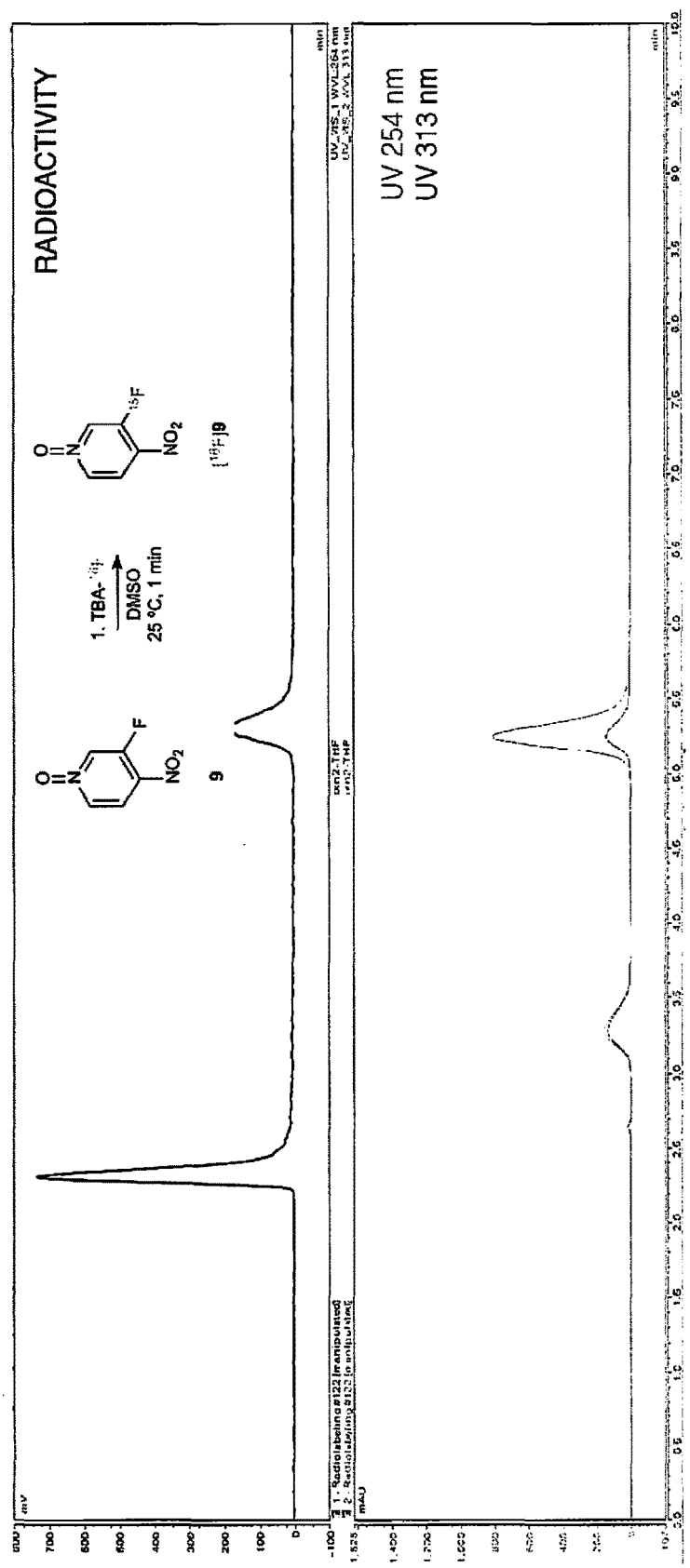
Figure 4A:
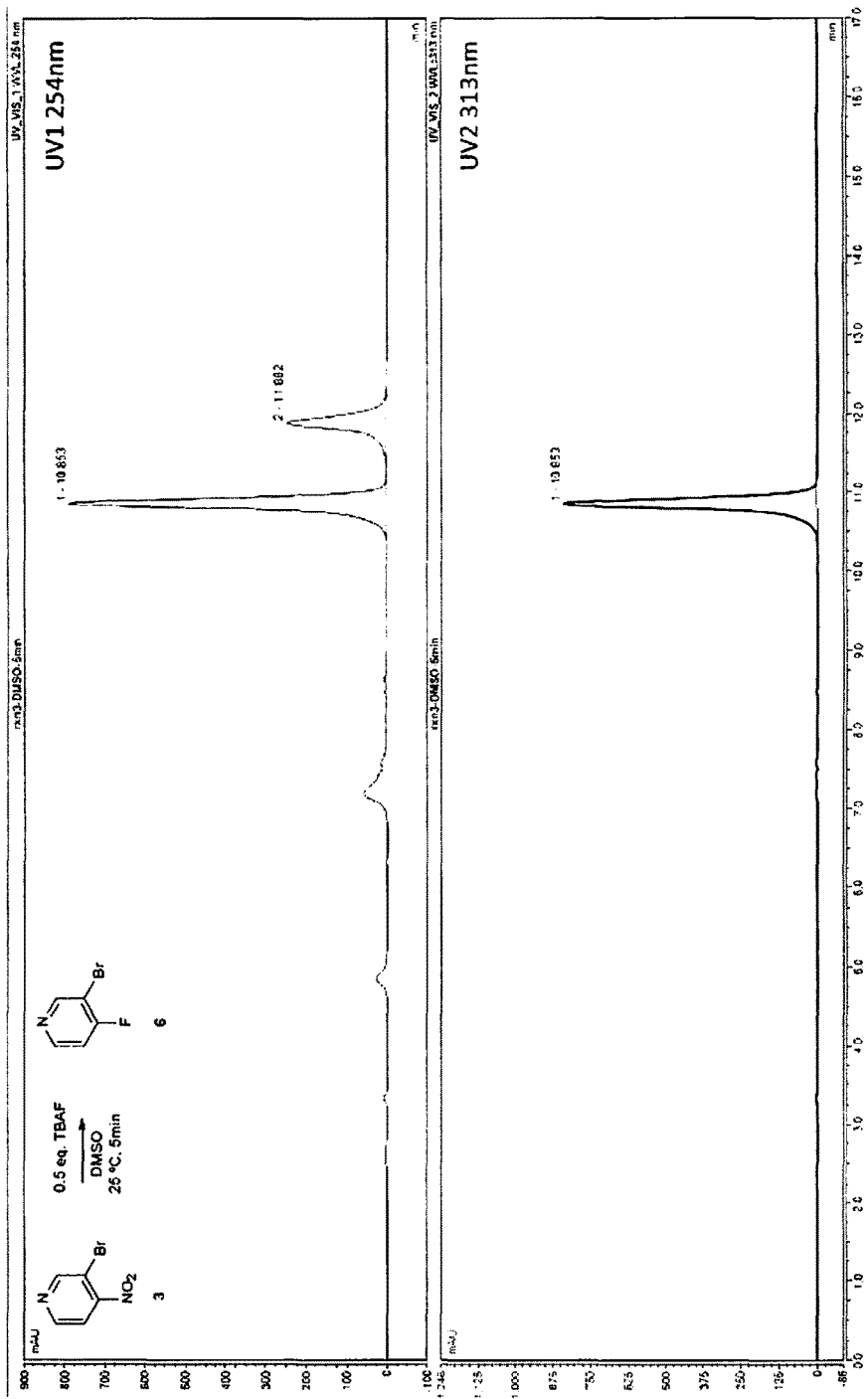
FIGS. 4A-4D Fluorination of 3-bromo-4-nitropyridine.
Figure 4B:
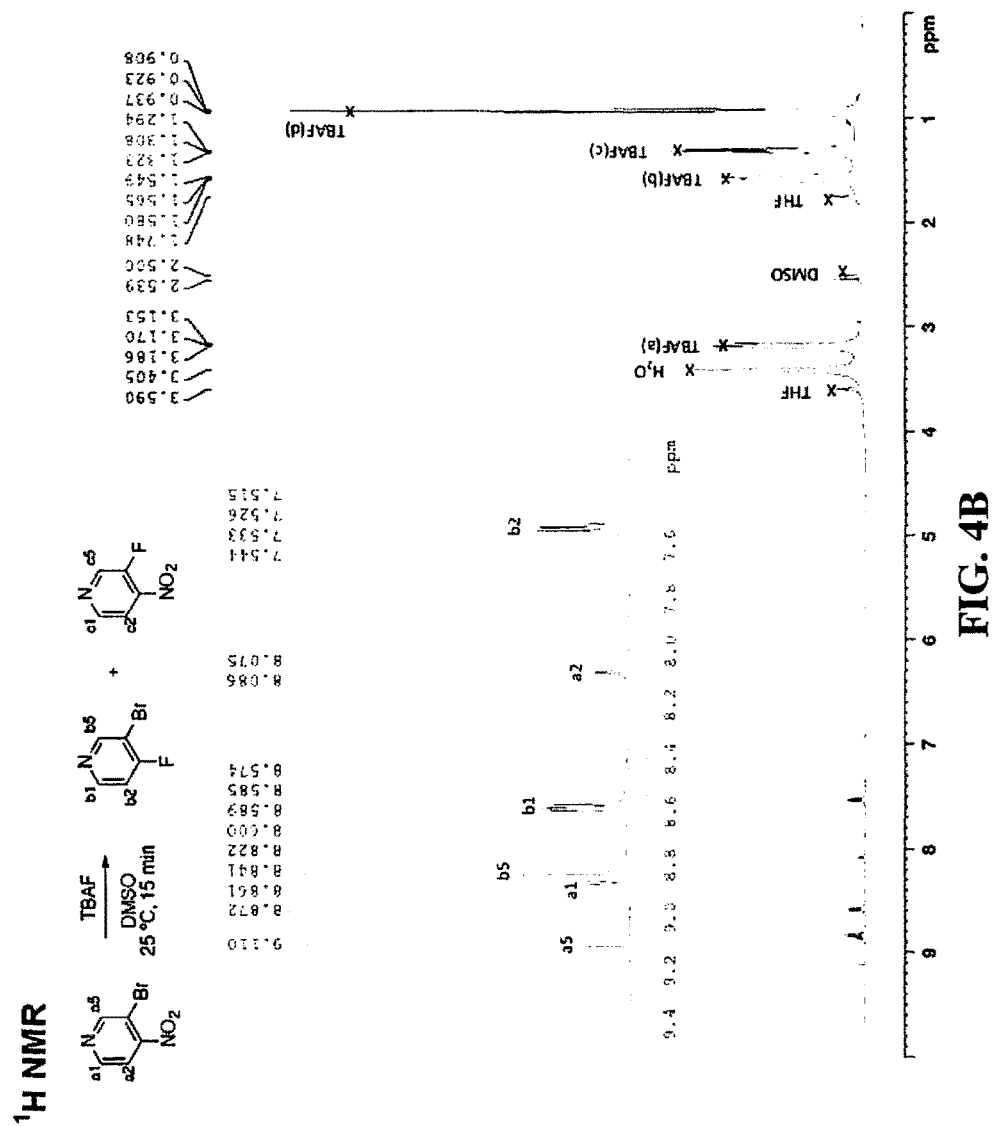
Figure 4C:
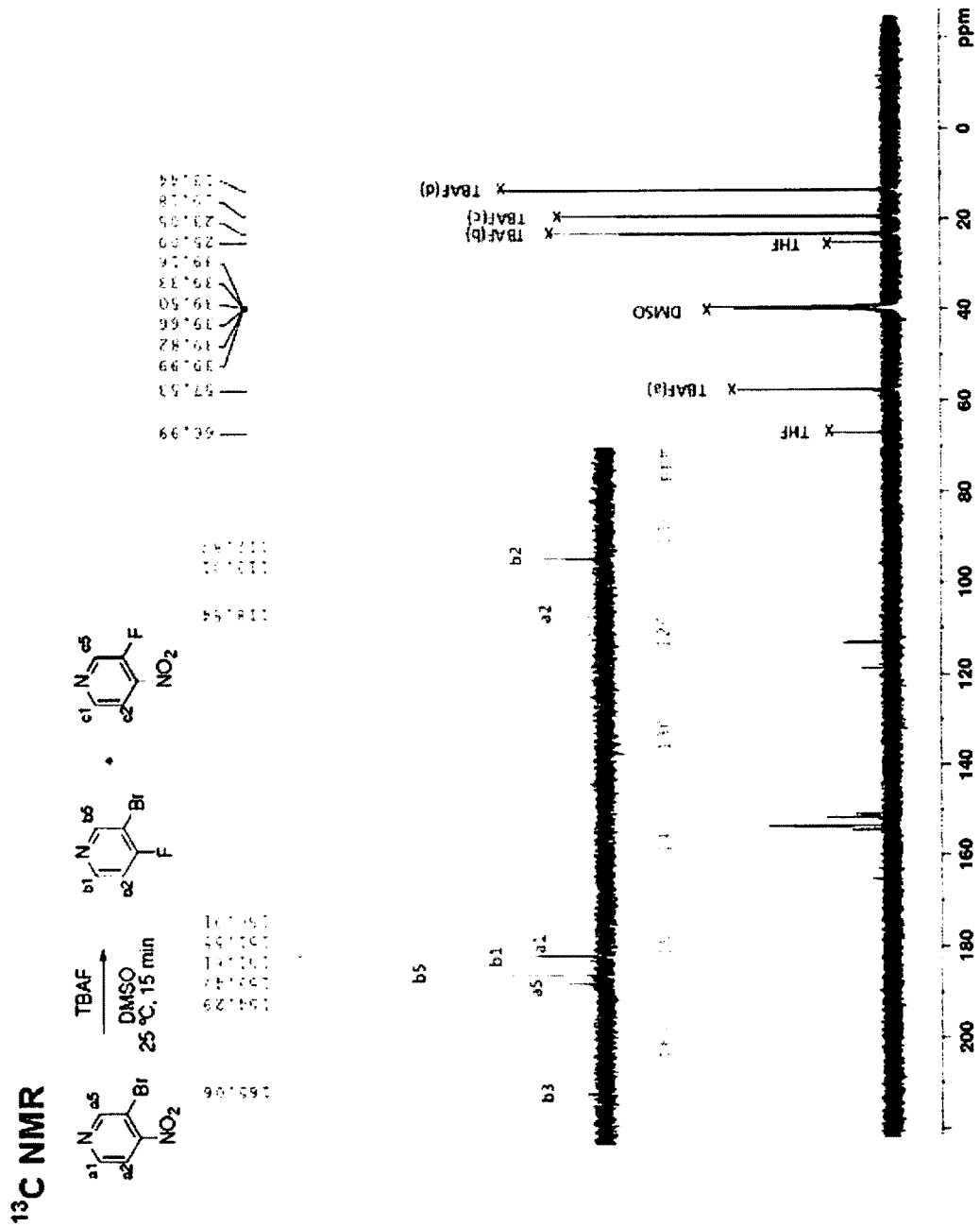
Figure 4D:
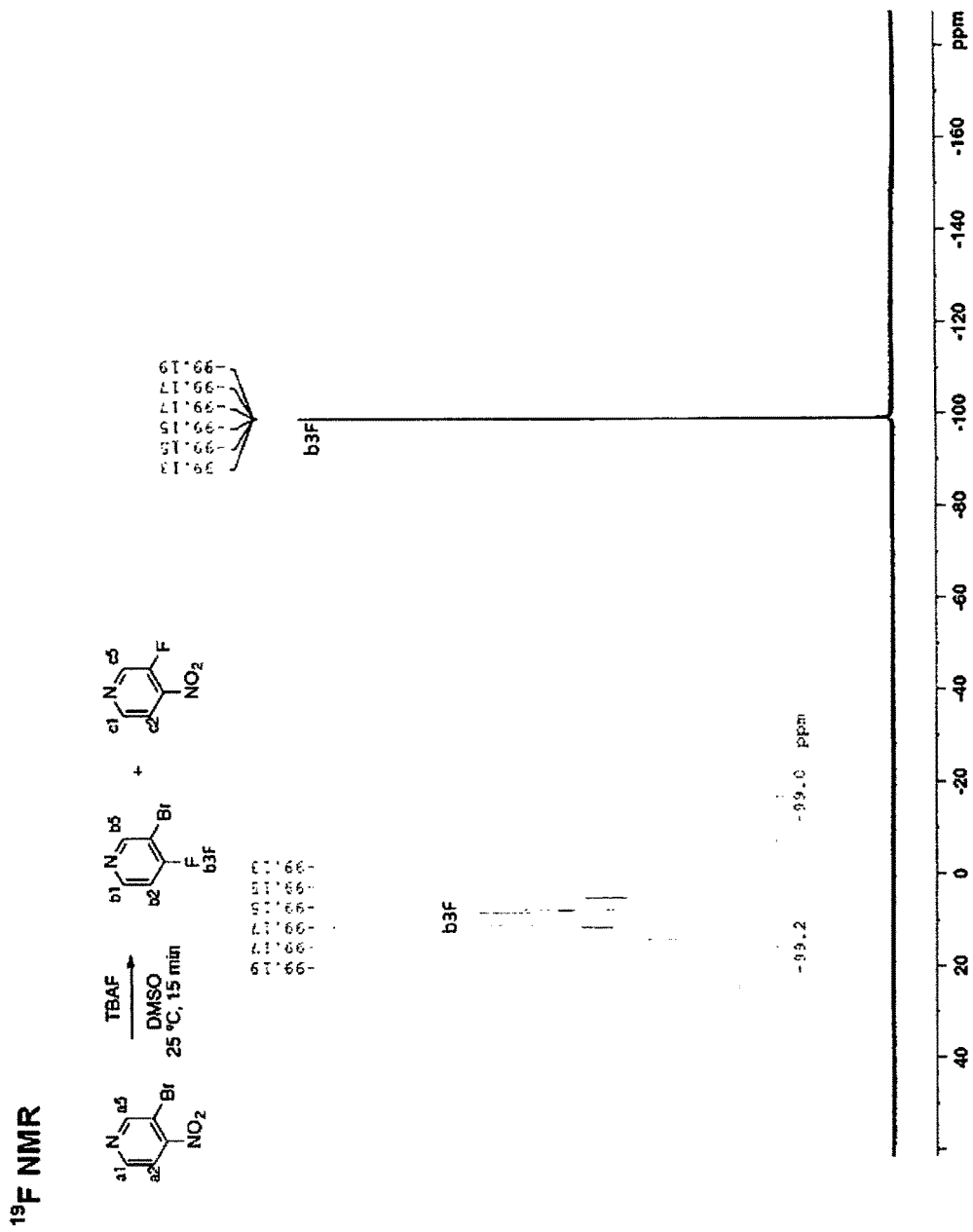
Figure 5A:
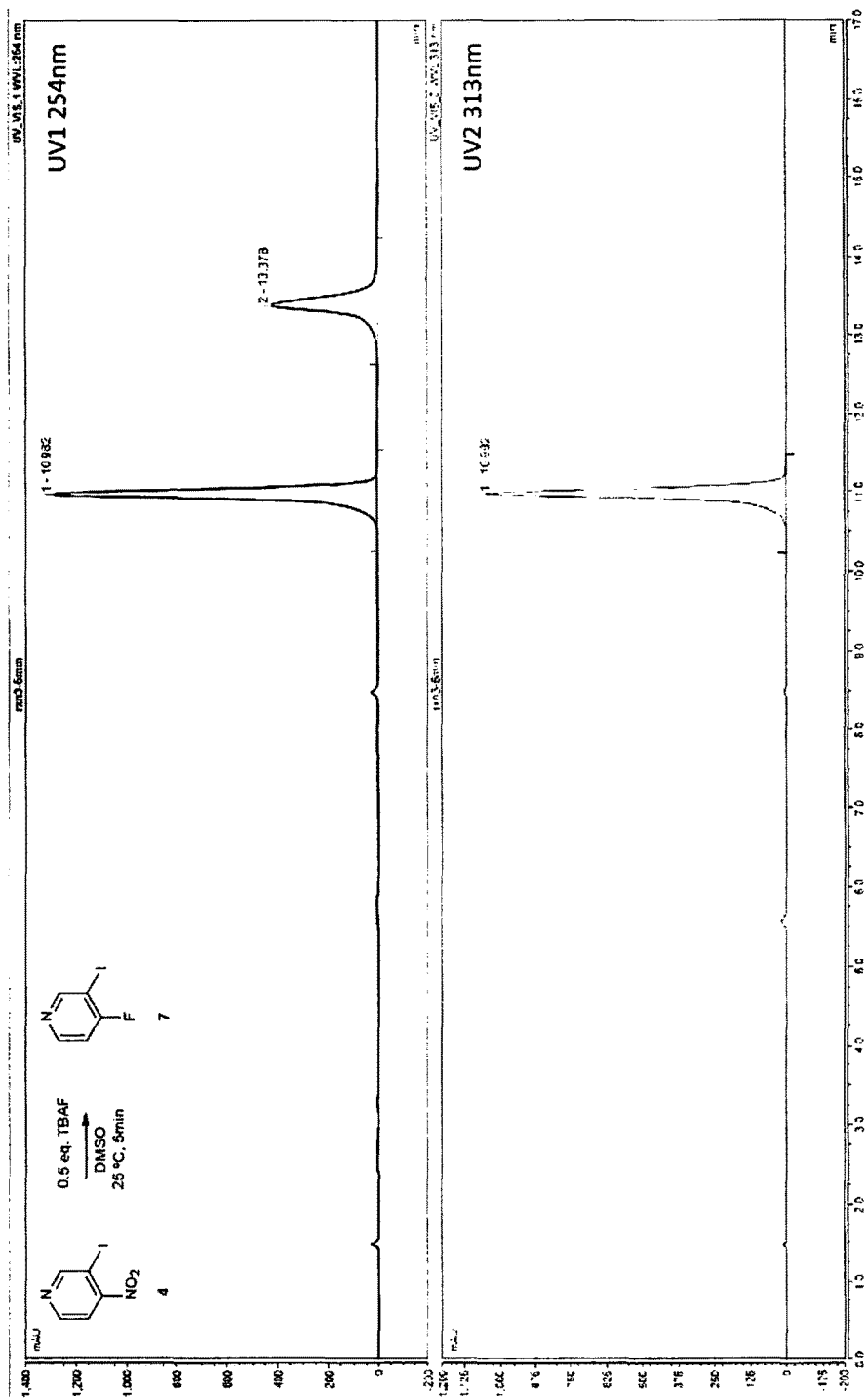
FIGS. 5A-5C Fluorination of 3-iodo-4-nitropyridine.
Figure 5B:
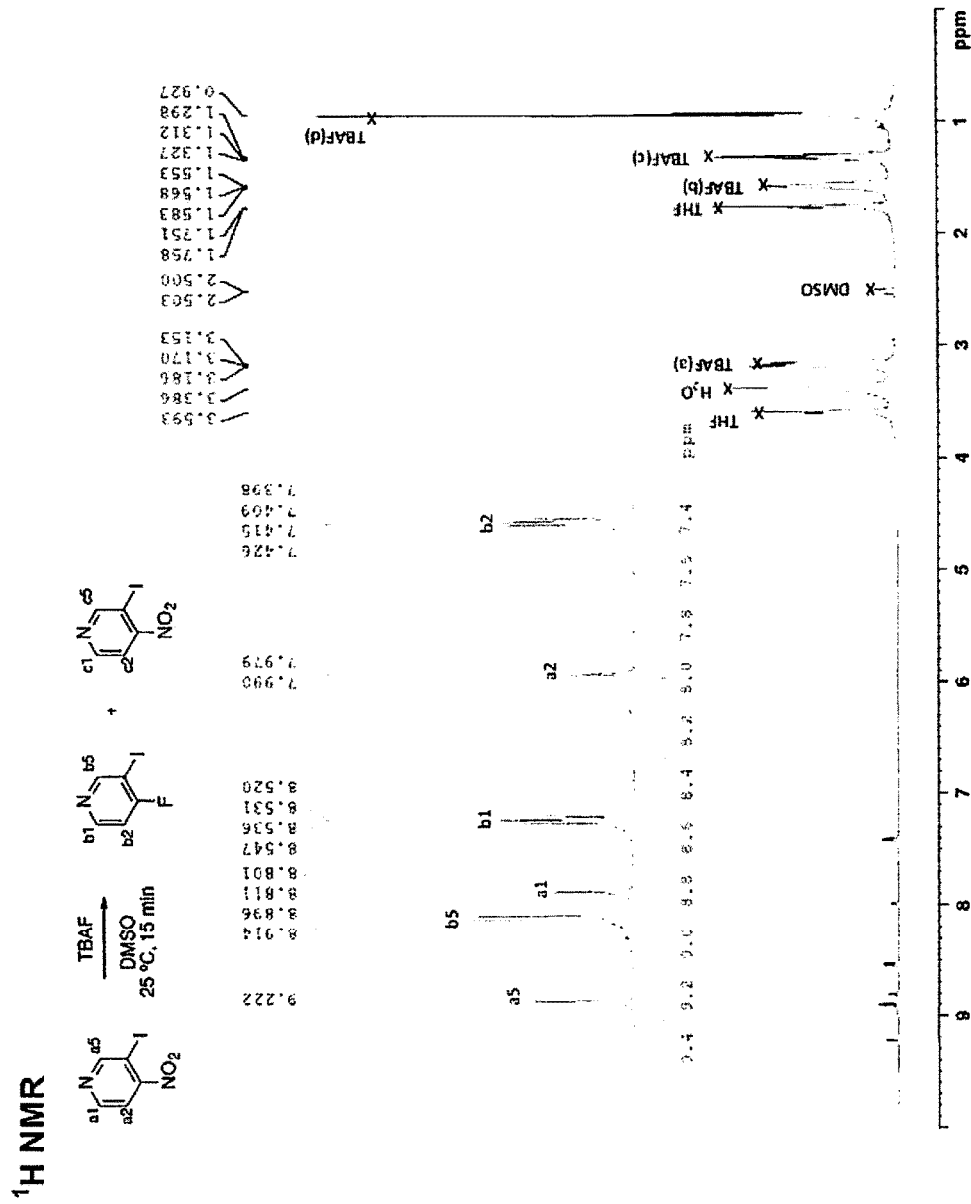
Figure 5C:
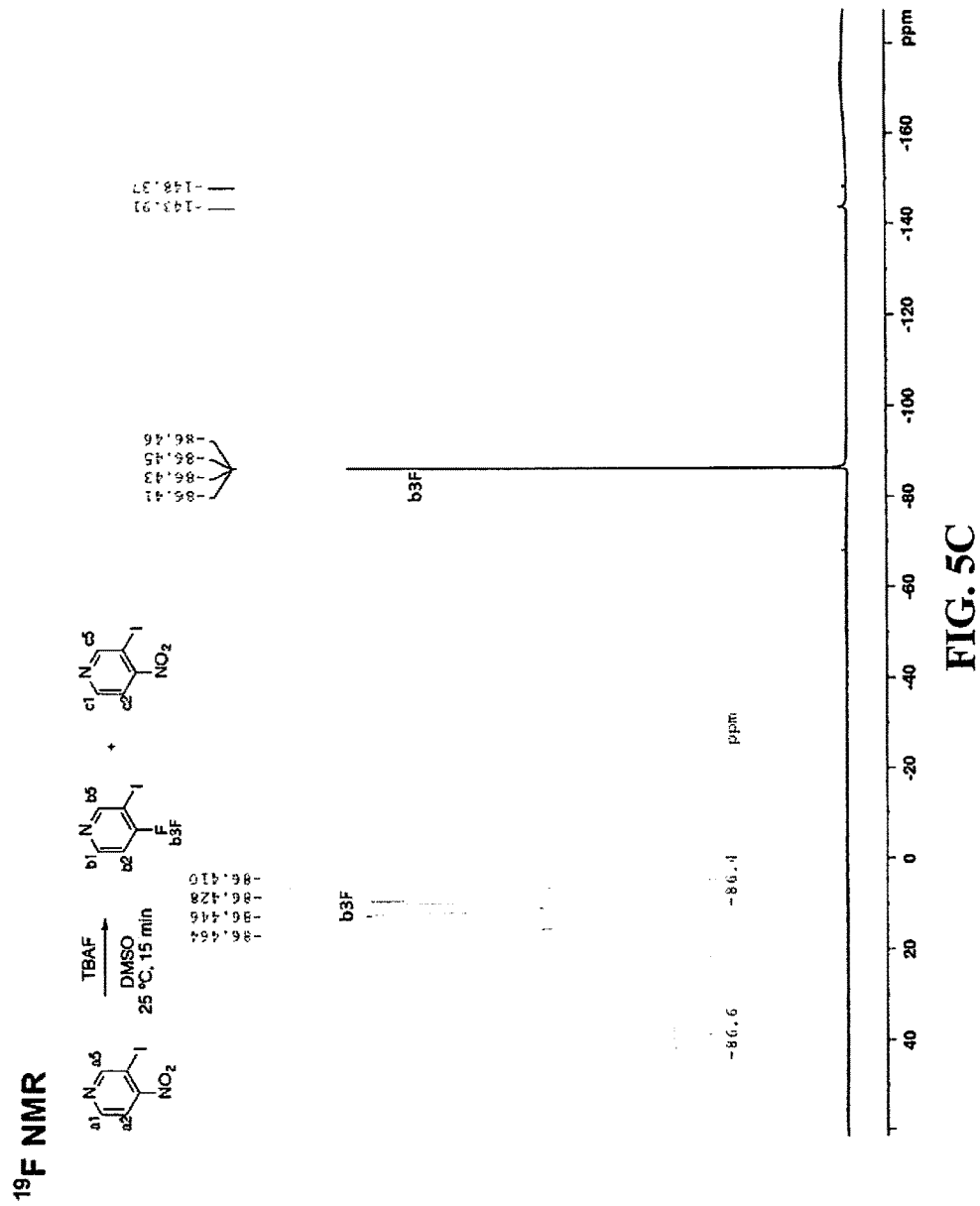

The second route A.2 involved fluorination of 3-bromo-4-nitropyridine (3) followed by reduction of the nitro group. Treatment of 3 with 0.5 equivalents of TBAF at room temperature produced the para-substituted produce 3-bromo-4-fluoropyridine (6) in 71.1±3.6% yield (relative to TBAF, n=4) as determined by HPLC and NMR (FIGS. 3B and 4A). Under these conditions, less than 0.2% of 3-fluoro-4-nitropyridine (5) was produced demonstrating a clear preference for the substitution to occur at the para- or nitro-position. Similar results were obtained with 3-iodo-4-nitropyridine (4) (FIGS. 5A-5B). This type of reactivity is expected from previously published data on nitro-substituted pyridines[2, 13] and consistent with the results from Abrahim et al.[5] who tested fluorination of a pyridine containing an ortho-nitro group and a meta-bromo group, and found exclusive substitution at the ortho-nitro position.

Figure 6A:
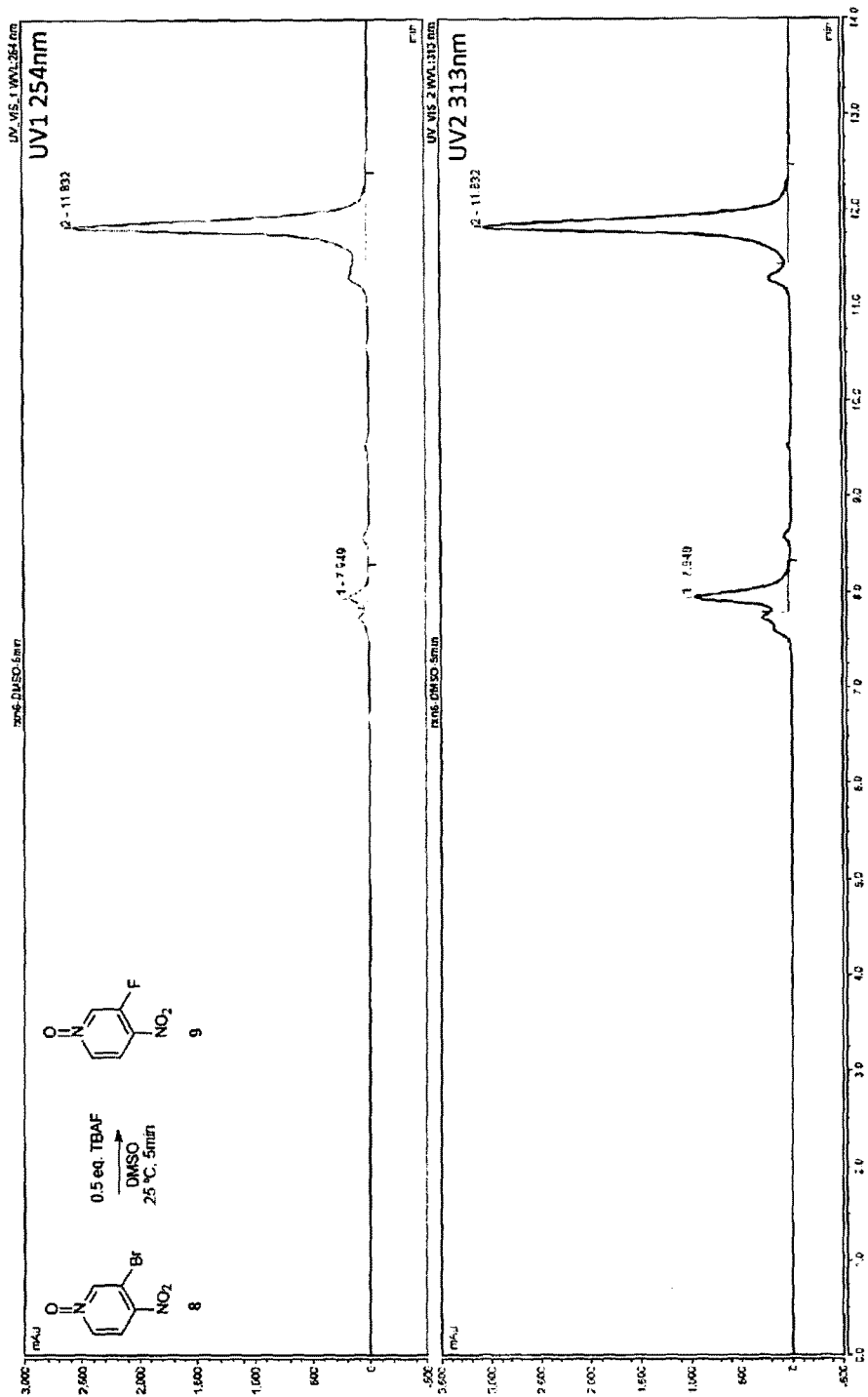
FIGS. 6A-6D Fluorination of 3-bromo-4-nitropyridine N-oxide.
Figure 6B:
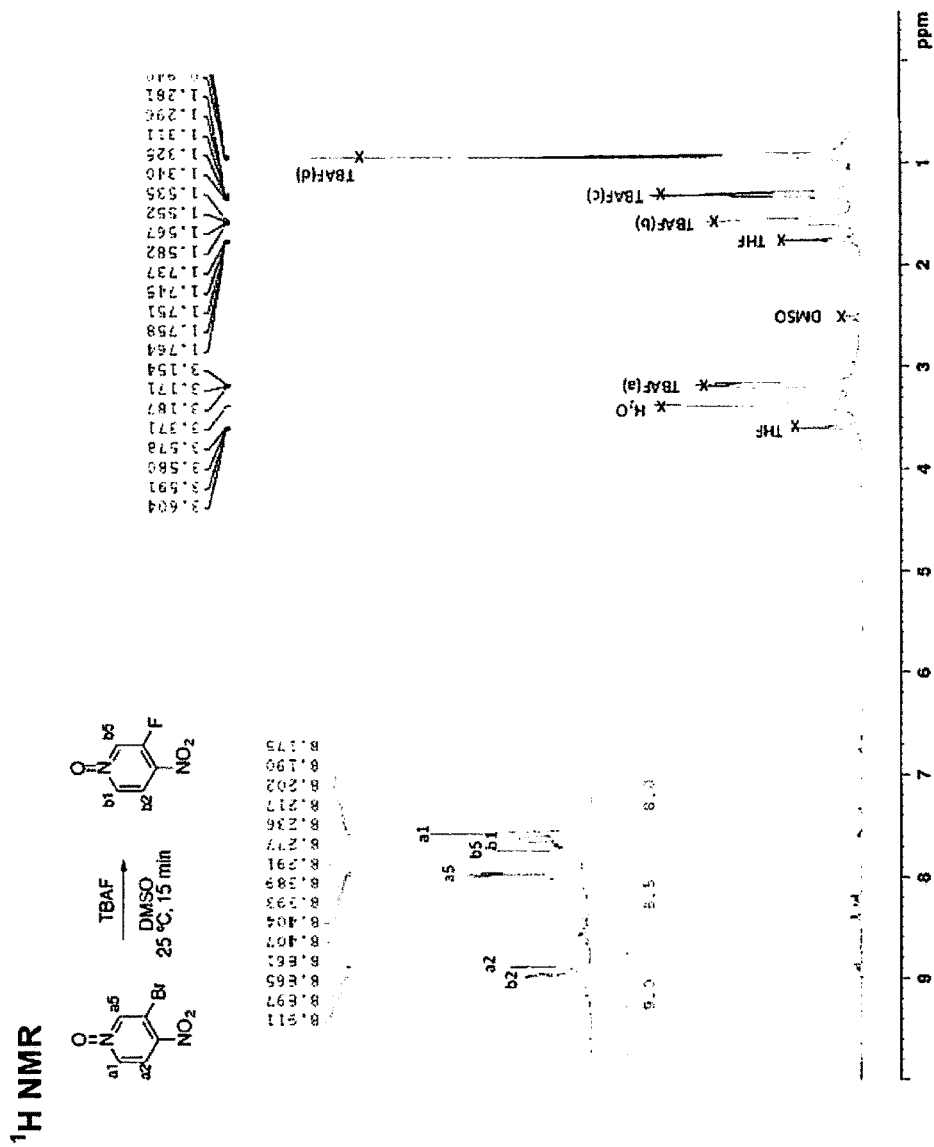
Figure 6C:
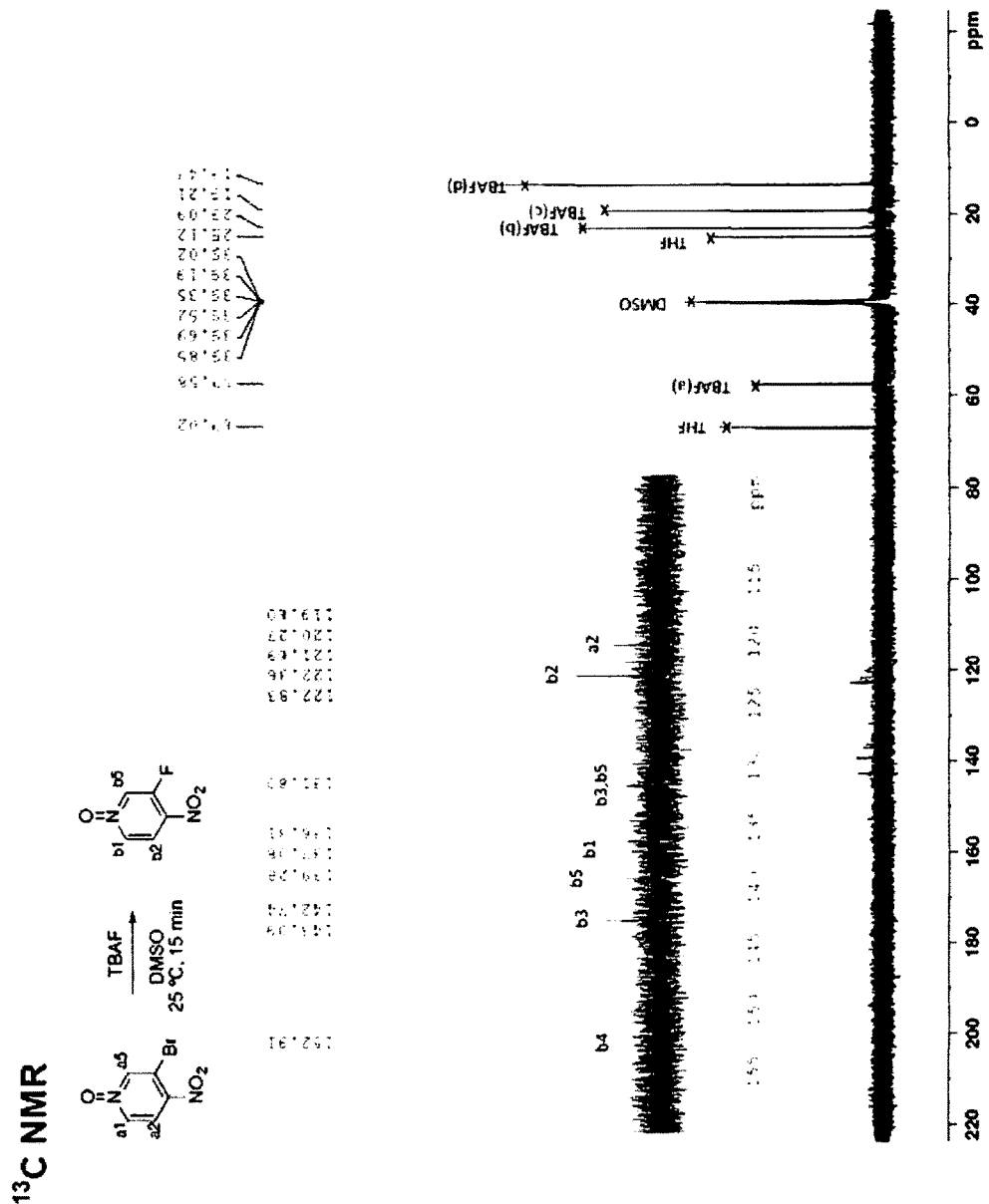
Figure 6D:
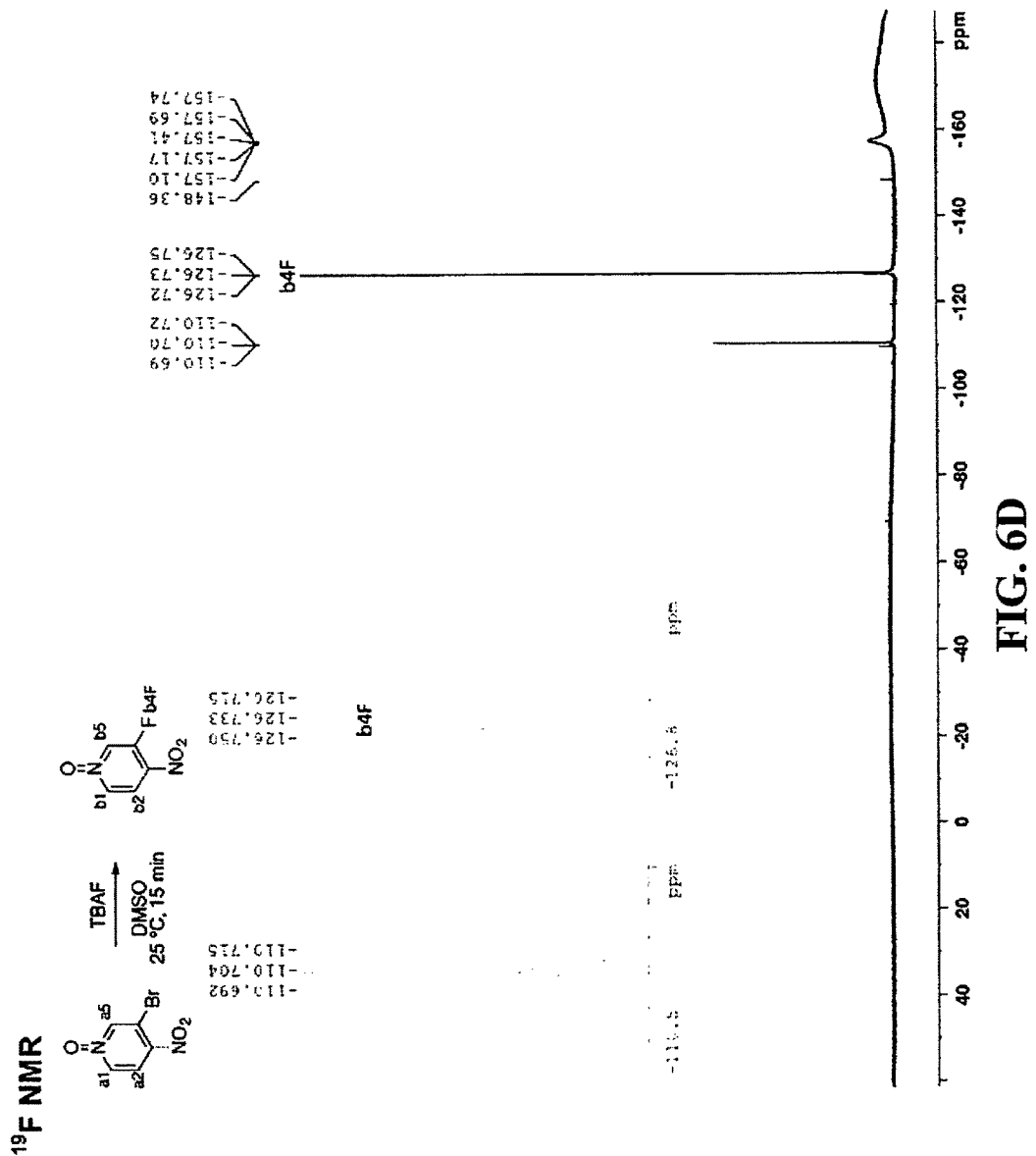

Fluorination of 3-bromo-4-nitropyridine N-oxide (8) was attempted, given the supposition that the electron withdrawing N-oxide would further increase the reactivity of the pyridine and result in fluorination at the meta-position (FIG. 1, route A3). In this case, treatment of 8 with 0.5 equivalents TBAF at room temperature produced the meta-fluorinated compound, 3-fluoro-4-nitropyridine N-oxide (9), as the main product in 20.7±2.7% yield (relative to TBAF, n=4) (FIGS. 6A-6B). Under these conditions, less than 2% fluorination at the para position was detected, indicating that the presence of the N-oxide group favors meta fluorination.

Figure 7A:
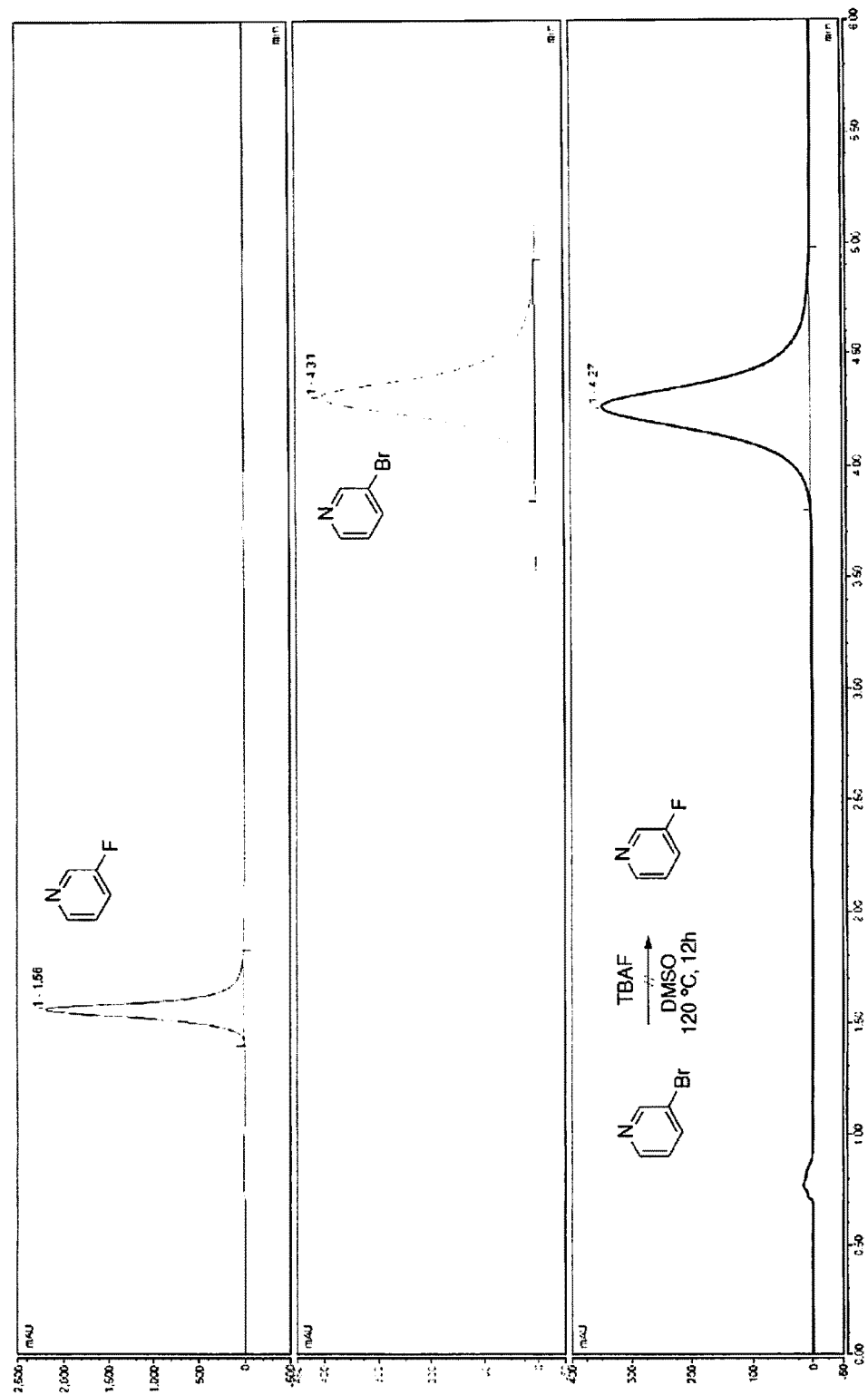
FIGS. 7A-7C Fluorination attempt of 3-bromopyridine.
Figure 7B:
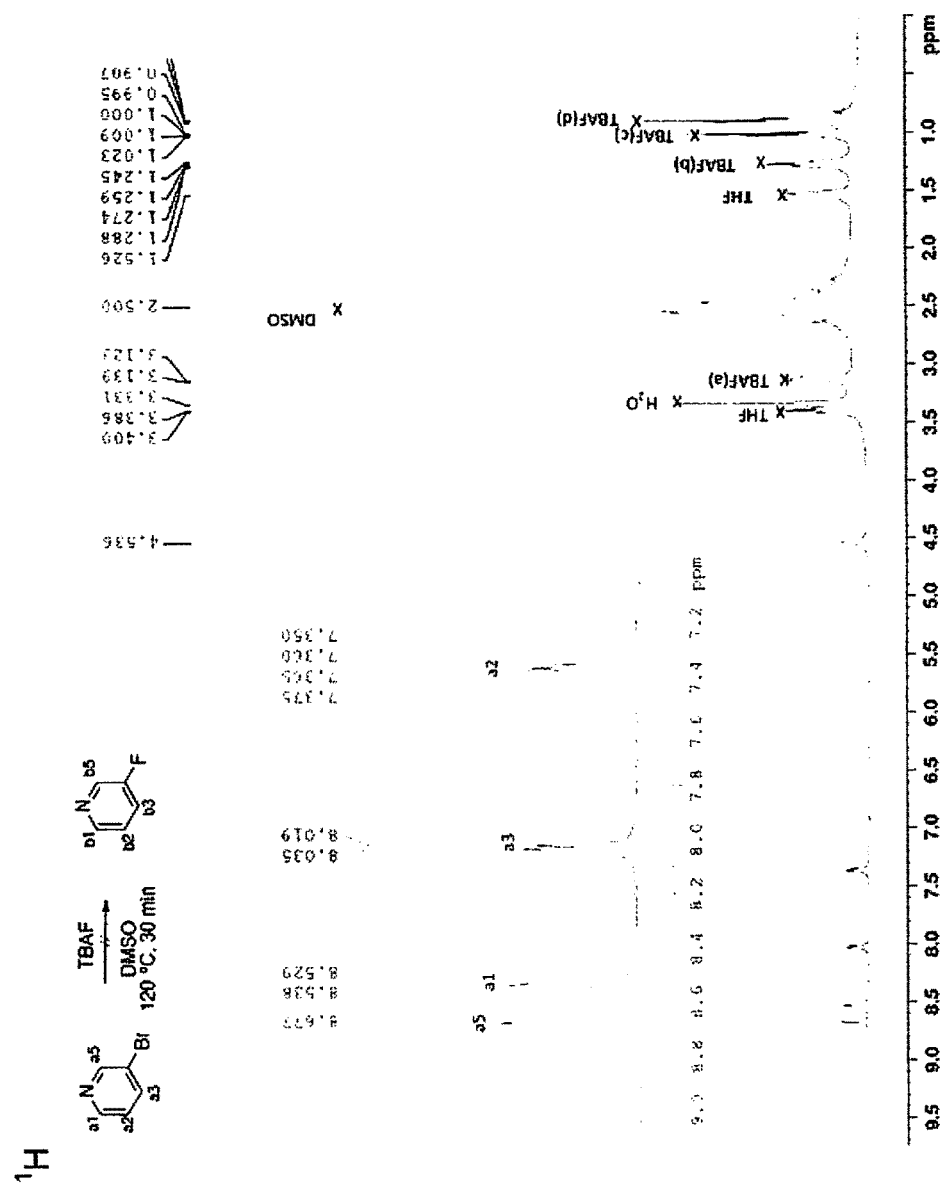
Figure 7C:
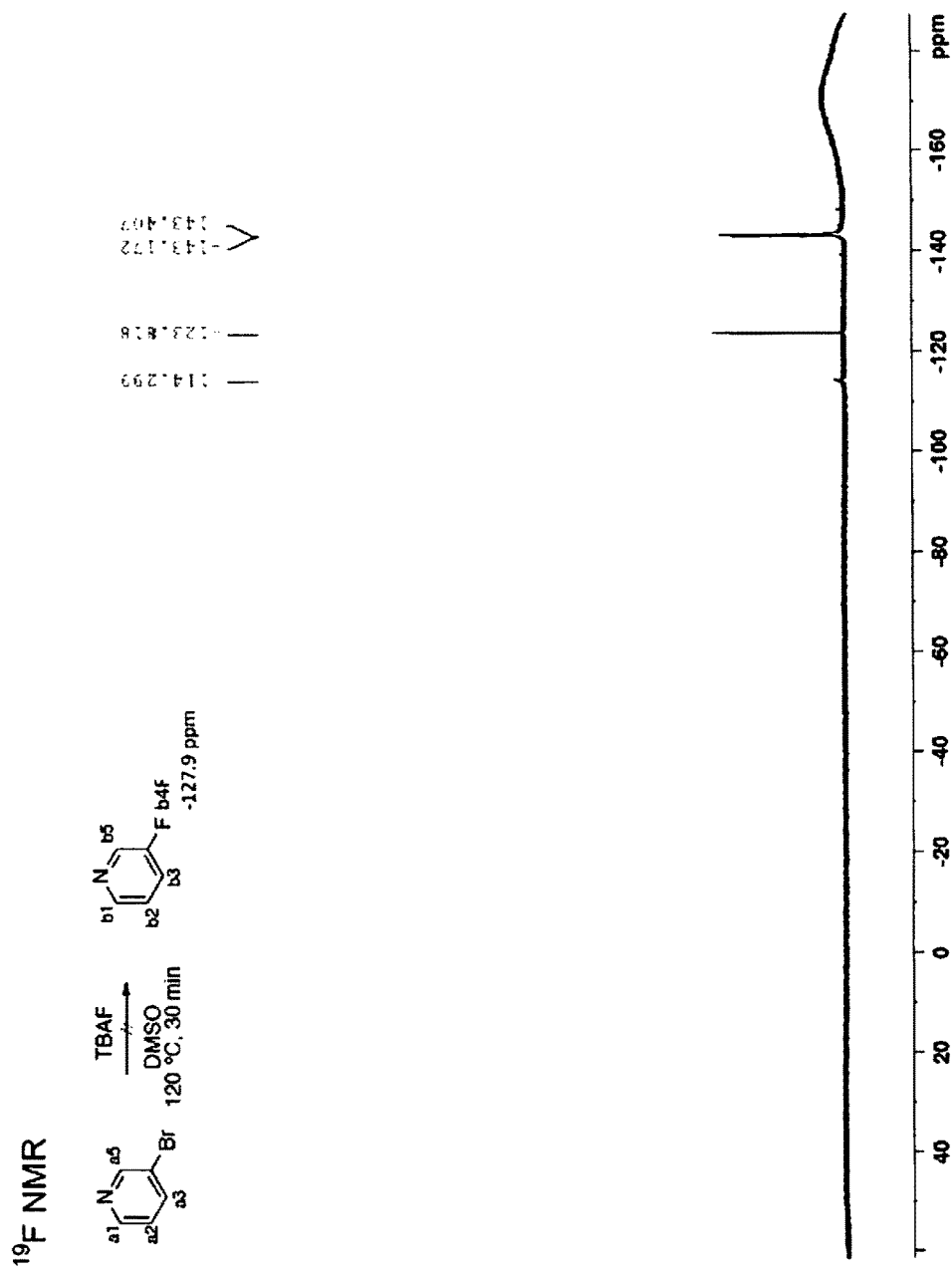
Figure 8A:
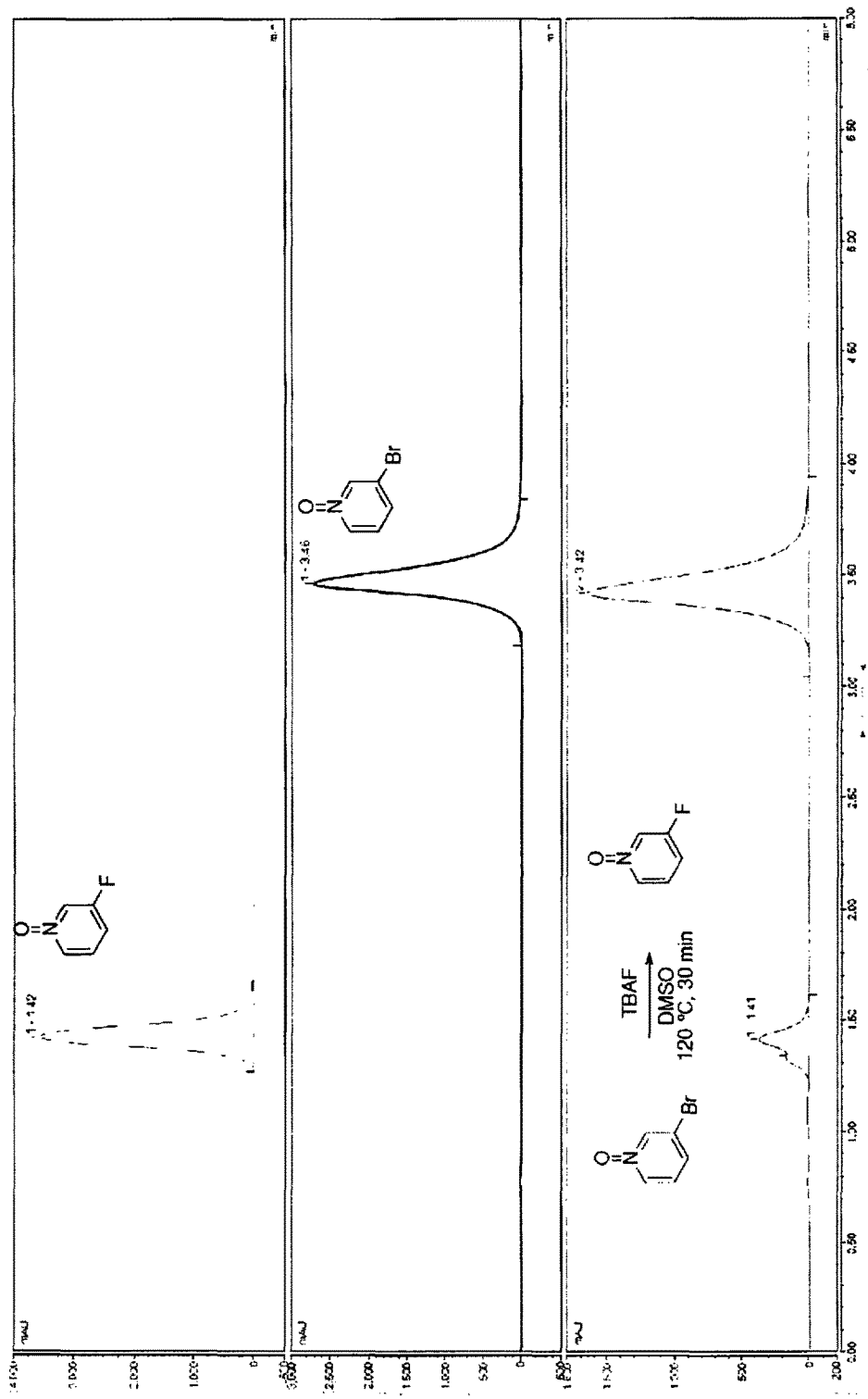
FIGS. 8A-8C Fluorination of 3-bromopyridine N-oxide.
Figure 8B:
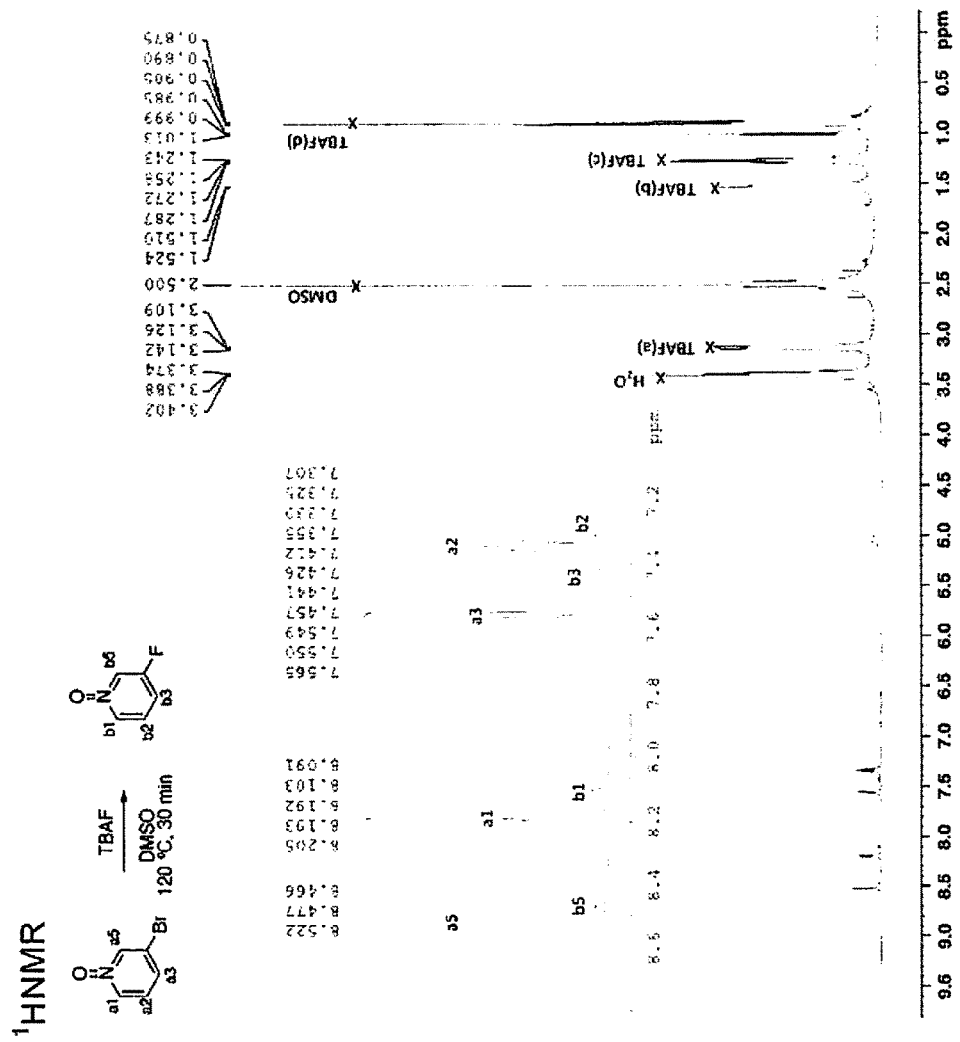
Figure 8C:
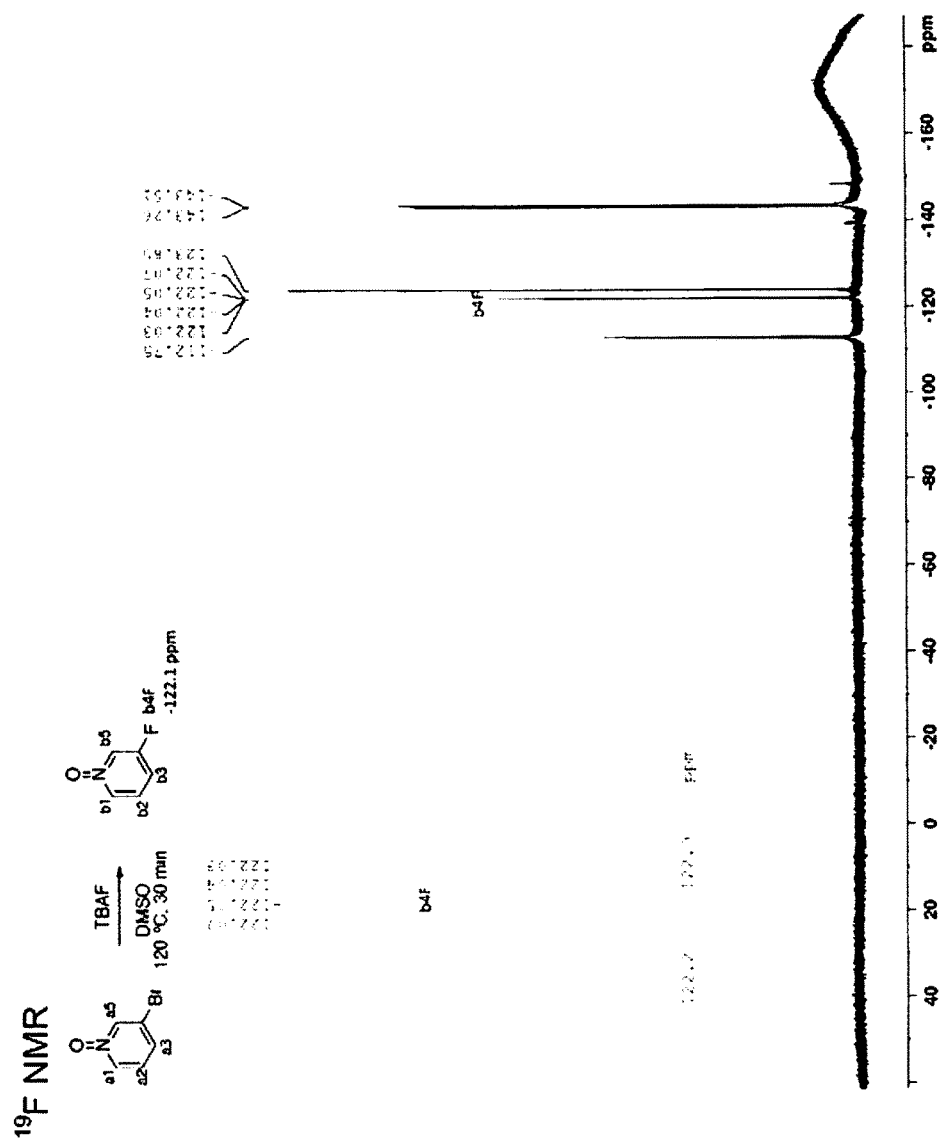

To examine the potential use of pyridine N-oxides as fluorination precursors, the reactivity of 3-bromopyridine and 3-bromopyridine N-oxide with TBAF was compared (FIGS. 2A-2B). 3-bromopyridine did not undergo reaction with 1.2 eq. of TBAF, despite reaction conditions of 120° C. for 12 hours (FIGS. 7A-7B). By contrast, over 25% conversion of 3-bromopyridine N-oxide was detected after 30 minutes at 120° C. (FIGS. 8A-8B). This result indicates that the para-nitro group's enhancement of pyridine reactivity (likely by lowering its activation energy), it is not sufficient to explain the reactivity and regioselectivity of the N-oxide towards fluorination. This regioselectivity is particularly surprising given early studies on the nucleophilic displacement of monosubstituted pyridine N-oxides by sodium ethoxide in ethanol, which round that the rate of displacement of nitro was 1,100-3,100 times larger than the bromo, and that the order of reactivity was 2>4>>3 position[14]. This difference may be due to the different nature of the nucleophile and solvation effects.

Figure 9A:
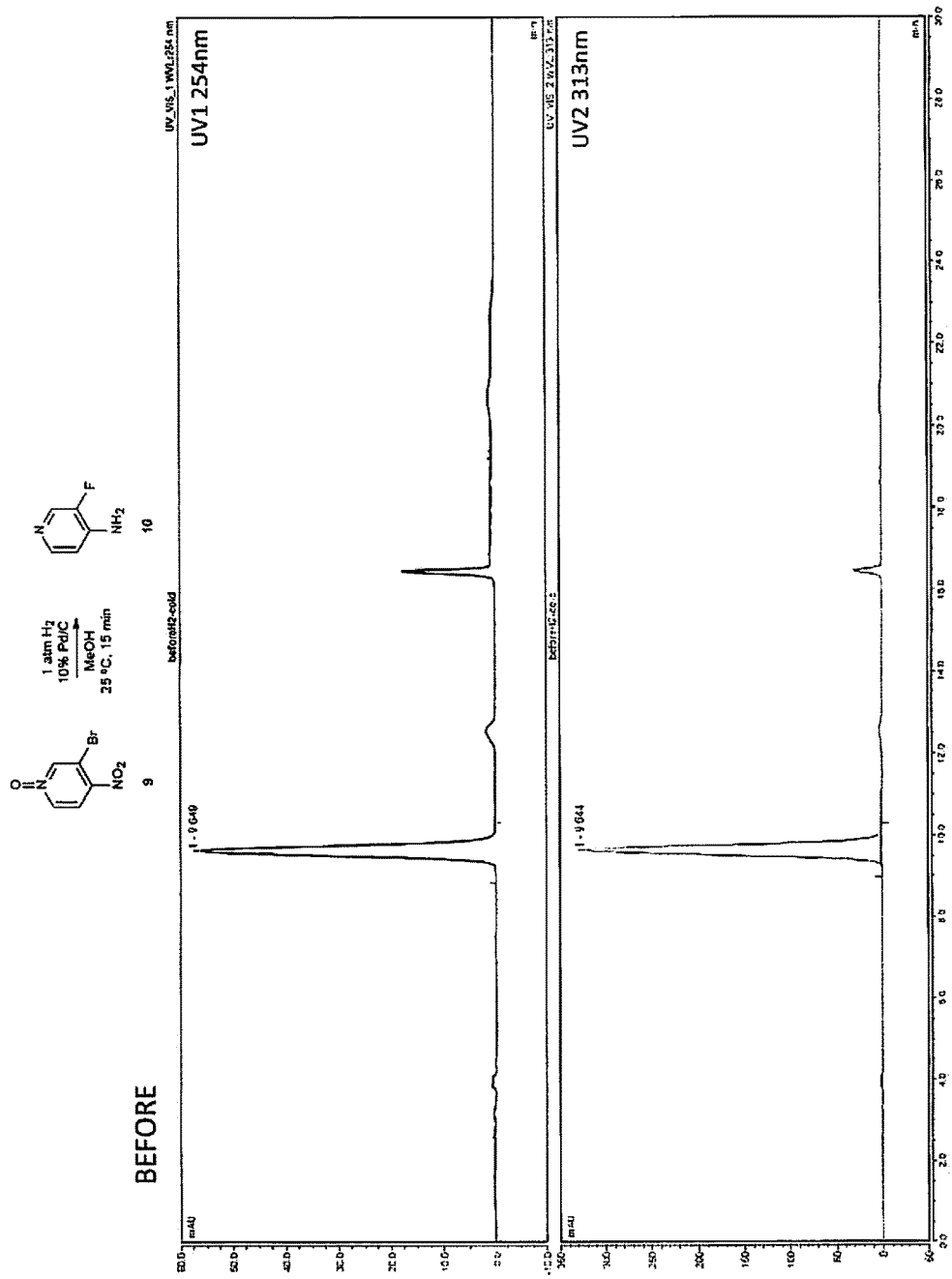
FIGS. 9A-9B Before and after UV HPLC traces of hydrogenation of 3-fluoro-4-nitropyridine N-oxide at 254 nm (top) and 313 nm (bottom). Starting material elutes at 9.6 min, product elutes at 10.1 min.
Figure 9B:
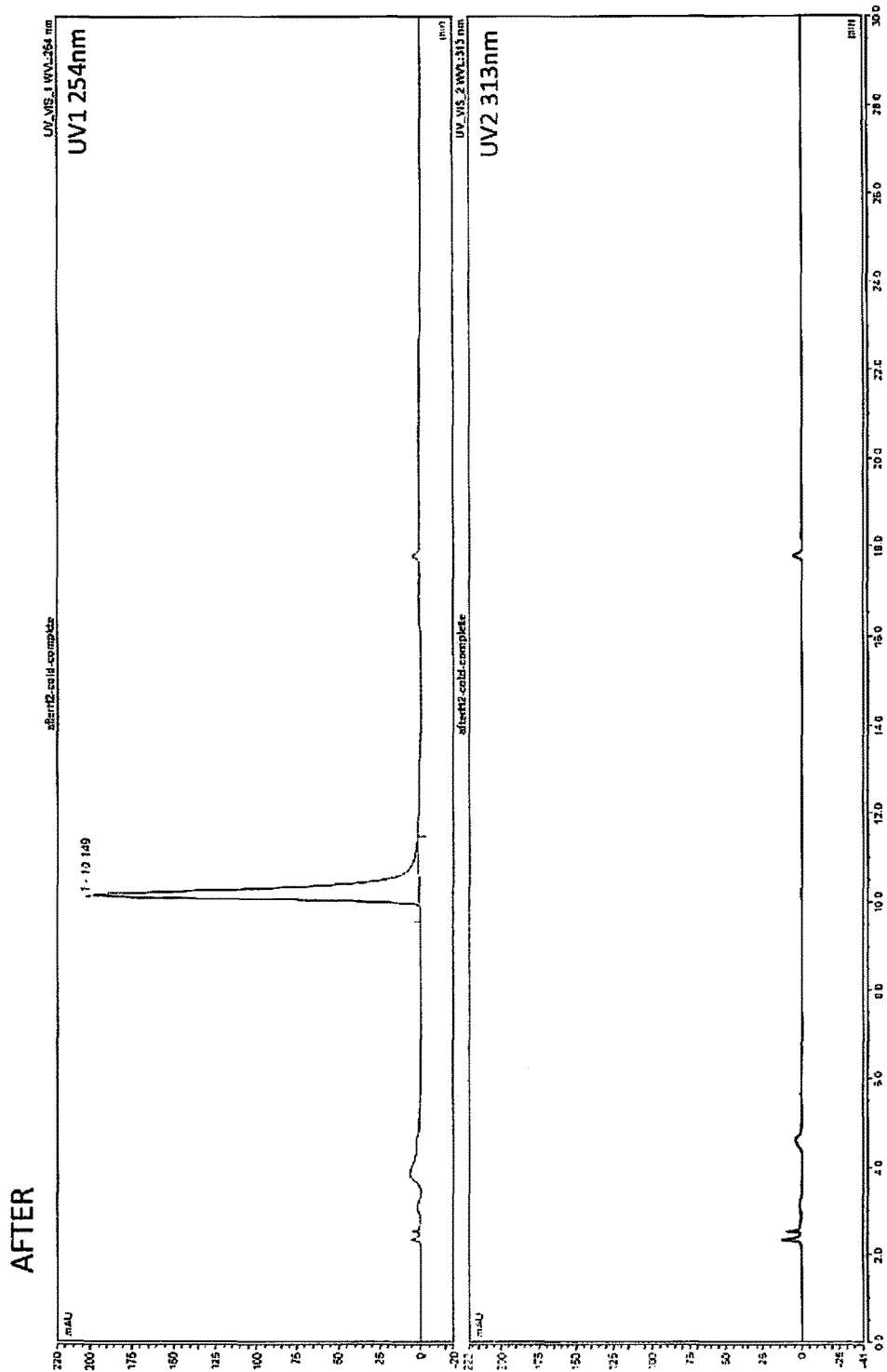

After obtaining compound 9, it was then reduced using standard hydrogenation conditions to generate the desired final product, 3-fluoro-4-aminopyridine (10) quantitatively (FIG. 9). Pyridine N-oxides have not previously been used as precursors for radiofluorination. This approach was further examined for the production of [$^{18}$F]-3-fluoro-4-aminopyridine.

Figure 3C:
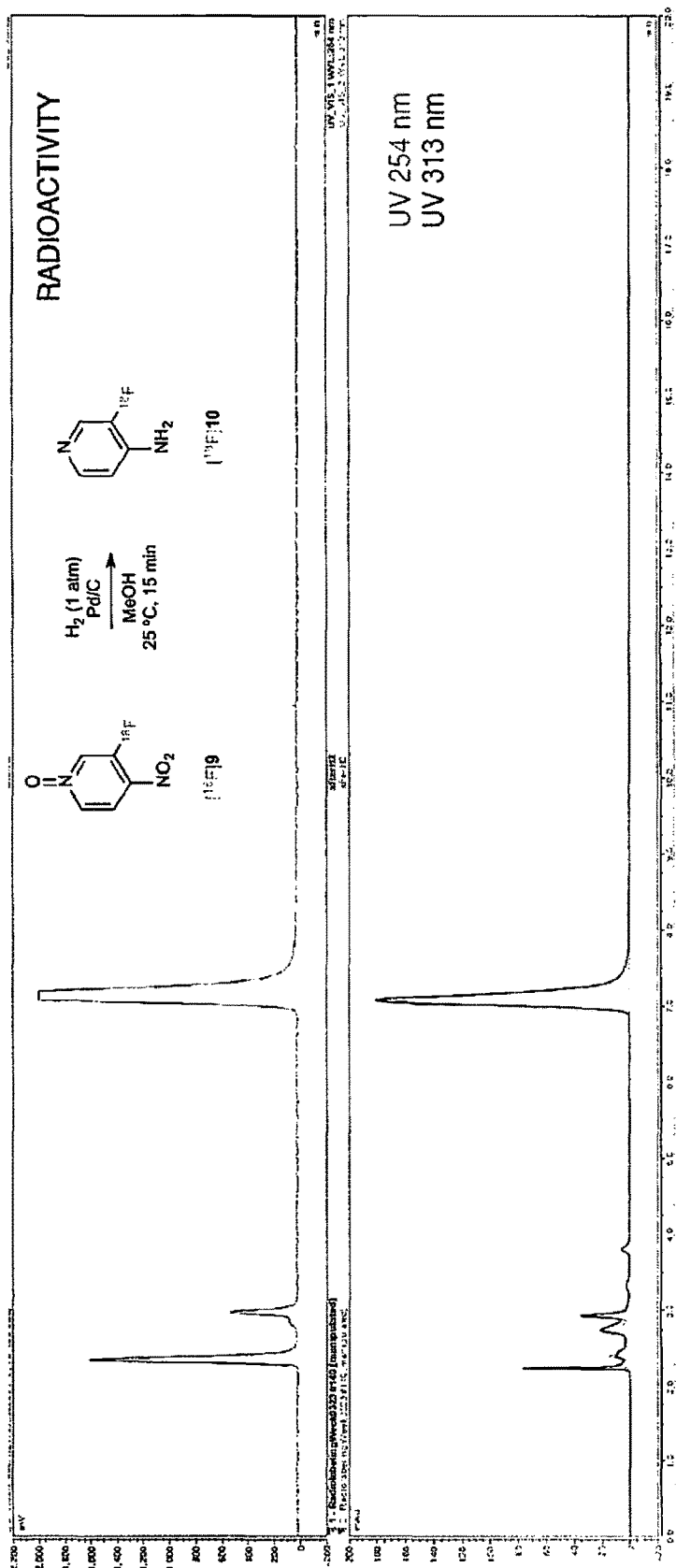
Figure 10:
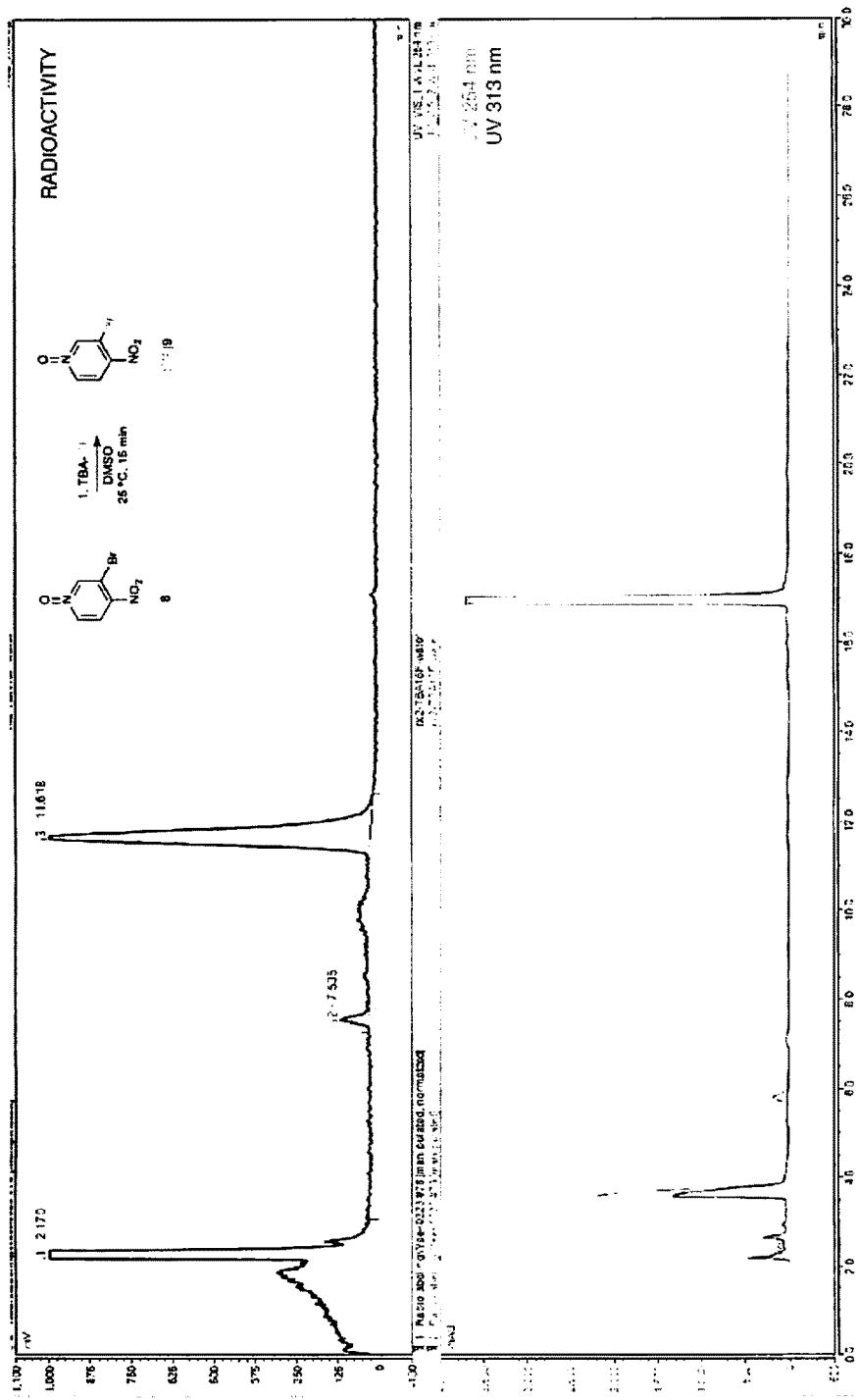
FIG. 10 Radioactive and UV HPLC trace of radiofluorination of 3-bromo-4-nitropyridine N-oxide (not spiked with reference standard). Starting material elutes at 17.2 min. and product elutes at 11.6 min.
Figure 11:
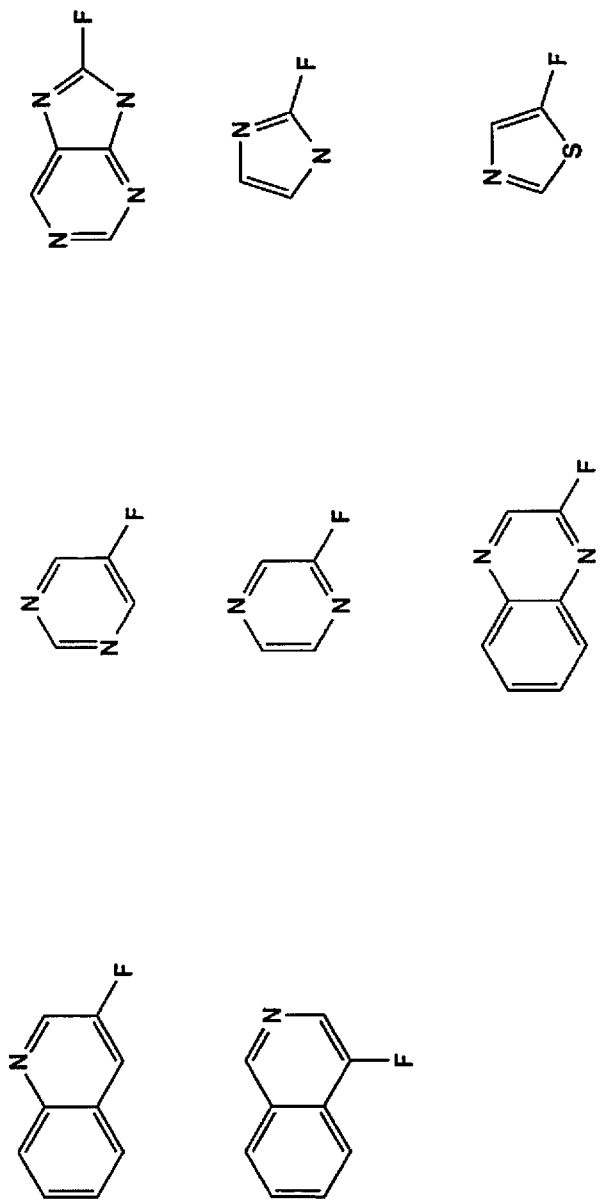
FIG. 11 Non-limiting examples of fluorinated aromatic N-heterocyclic compounds that may be synthesized by the inventive methods.

Radiochemical synthesis of [$^{18}$F]-3-fluoro-4-aminopyridine was conducted as shown in FIG. 3C. The procedure was similar to the non-radioactive synthesis described above except that [$^{18}$F]-TBAF was prepared immediately before the reaction by trapping [$^{18}$F]-fluoride in a strong anion exchange cartridge and eluting it with TBA-HCO$_3$. The reaction was carried out in DMSO at room temperature. After 15 min, HPLC analysis of the reaction crude showed an early peak that elutes with the solvent front corresponding to unreacted [$^{18}$F]-TBAF and a main peak corresponding to the desired product (FIG. 10). Under the test conditions, the isolated decay-corrected yield for the desired product was 10.4±1.8% (n=8). Upon further characterization, co-injection of the reaction crude with a small amount of reference standard consistently gave higher yields (25±4%, decay corrected, n=8) (FIG. 3A). This led to the hypothesis that the non-radioactive 3-fluoro-4-nitropyridine N-oxide (9) could be contributing to the radiolabeling yield by $^{19}$F/$^{18}$F exchange.

Figure 2A:
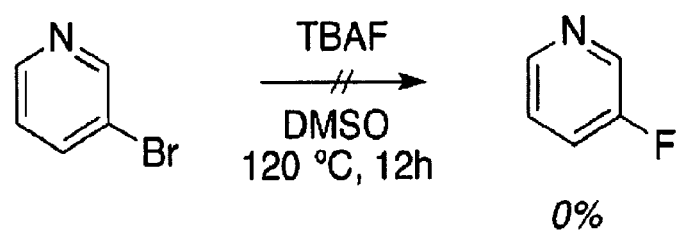
FIGS. 2A-2C.
Figure 2B:
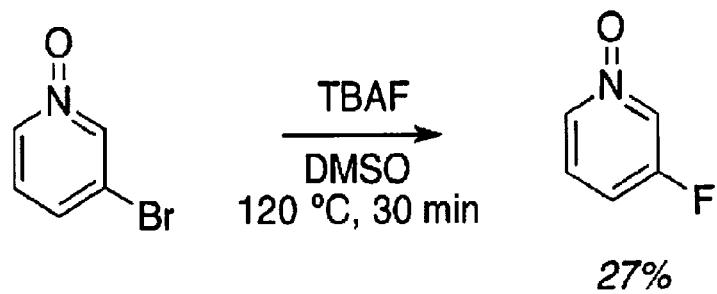
Figure 2C:
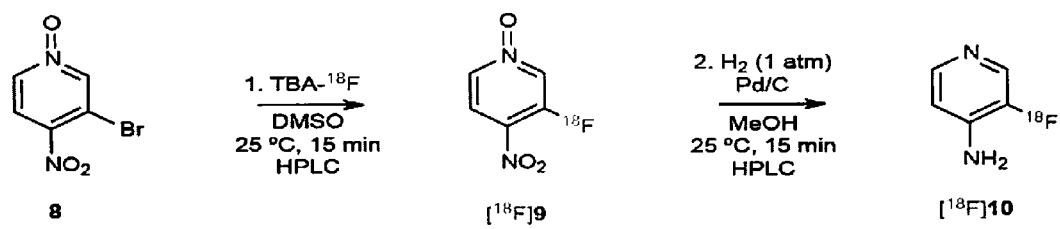

Labeling of 3-fluoro-4-nitropyridine N-oxide was examined with [$^{18}$F]-TBAF in the absence of the bromo precursor we obtained 33.1±5.4% (n=4) decay-corrected isolated yield (FIG. 2A). This reaction reaches equilibrium within seconds. Fluorine exchange in organic compounds has been reported before[15], however, this is the first example of fluoride exchange of a C—F bond in a heterocyclic compound.

EXAMPLES

Example 1

Non-radioactive fluorination of 3-bromo-4-nitropyridine (3): 10 µL of 1 M tetrabutylammonium fluoride (TBAF) solution in THF (10 µmol, 0.5 eq.) was added to a solution of 3-bromo-4-nitropyridine (96%, Aurum Pharmatech, LLC) (20 µmol, 1 eq.) in 500 µL of anhydrous dimethylsulfoxide (DMSO) in a 2 mL HPLC vial. The reaction was analyzed by HPLC (conditions A). Retention times: 3-bromo-4-nitropyridine (3)=10.83 min, 3-fluoro-4-nitropyridine=8.38, 3-bromo-4-fluoropyridine (6)=11.76 min. Retention times for the product matched within 0.05 min the reference standard. Identity of the product was confirmed by HR-MS (m/z M$^+$ exp.: 174.9423, calc: 174.9433) and $^1$H, $^{13}$C and $^{19}$F NMR. Product amount was calculated from the area under the curve of the HPLC UV1 trace using a calibration curve.

Example 2

Non-radioactive fluorination of 3-iodo-4-nitropyridine (4): 10 µL of 1 M TBAF solution in THF (10 µmol, 0.5 eq.) was added to a solution of 3-iodo-4-nitropyridine (96%, Aurum Pharmatech, LLC) (20 µmol, 1 eq.) in 500 µL of anhydrous dimethylsulfoxide (DMSO) in a 2 mL HPLC vial. The reaction was analyzed by HPLC (conditions A). Retention times: 3-iodo-4-aminopyridine (4)=11.02 min, 3-iodo-4-fluoropyridine (7)=13.43 min. Starting material absorbs at 254 and 313 nm. Product does not absorb at 313 nm. Identity of the product was confirmed by HR-MS (m/z M$^+$ exp.: 222.9288, calc: 222.9294) and $^1$H, $^{13}$C and $^{19}$F NMR.

Example 3

Non-radioactive fluorination of 3-bromo-4-nitropyridine N-oxide (8): 10 µL of 1 M TBAF solution in THF (10 µmol, 0.5 eq.) was added to a solution of a 3-bromo-4-nitropyridine N-oxide (98+%, Alfa Aesar) (20 µmol, 1 eq.) in 500 µL of anhydrous DMSO in a 2 mL HPLC vial. The reaction was analyzed by HPLC (conditions B). Retention times: 3-bromo-4-nitropyridine N-oxide (8)=11.84 min, 3-fluoro-4-nitropyridine N-oxide (9)=7.93 min. Retention time for the product matched within 0.05 min the reference standard. Identity of the product was confirmed by HR-MS (m/z M+ exp.: 158.0141, calc.: 158.0128) and $^1$H, $^{13}$C and $^{19}$F NMR. Product amount was calculated from the area under the curve of the HPLC UV2 trace using a calibration curve.

Example 4

Catalytic hydrogenation of 3-fluoro-4-nitropyridine N-oxide (9): 0.1 mg of 3-fluoro-4-aminopyridine N-oxide (9) was dissolved in 4 mL of MeOH in a 50 mL round bottom flask containing a stir bar. While stirring, 3-4 mg of 10% Pd/C (dry basis) was added and the flask sealed with a rubber septum. The vial was evacuated and backfilled with hydrogen gas from a balloon and the mixture was allowed to react for 10 min. After 10 min, the suspension was passed through a 0.4 µm PTFE filter and analyzed by HPLC (conditions C). Reference retention times: 3-fluoro-4-aminopyridine N-oxide (9)=5.80 min, 3-fluoro-4-aminopyridine (10)=7.05 min. Retention time for the product matched within 0.05 min the reference standard. Identity of the product was confirmed by HR-MS (m/z M+ exp.: 112.0416, calc: 112.0437). Product amount was calculated from the area under the curve of the HPLC UV2 trace using a calibration curve.

Example 5

Production of tetrabutyl ammonium [$^{18}$F]-fluoride ([$^{18}$F]-TBAF): Fifty to a hundred mCi (1.85-3.7 GBq) of cyclotron-produced $^{18}$F was trapped in a Sep-Pak Accell Plus QMA Plus Light Cartridge (Waters Corporation) preconditioned with 5 mL of 50 mM of KHCO$_3$ followed by 10 mL of water and 20 mL of air. The cartridge was eluted with a solution containing of 300 µL of 50 mM TBA-HCO3 in water with 5% EtOH (ABX advanced biochemical compounds GmbH) and 600 µL of acetonitrile (MeCN). The water-MeCN solution was dried azeotropically at 85° C. under reduced pressure (20 mbar) for 7.5 min. To ensure complete dryness, two additional aliquots of MeCN (500 µL) were added, followed by evaporation (3 min). After drying, the vial was filled with argon gas and cooled down to room temperature in a water beaker. The [$^{18}$F]-TBAF residue was dissolved in 100-400 µL of anhydrous DMSO and used for the reactions.

Example 6

Radiochemical synthesis of [$^{18}$F]-3-fluoro-4-nitropyridine N-oxide ([$^{18}$F]-9) from 3-bromo-4-nitropyridine N-oxide (8): 100 µL of 3-bromo-4-nitropyridine N-oxide (8) dissolved in DMSO (20 mg/mL) were added to 100 µL of [$^{18}$F]-TBAF solution (~10 mCi, ~370 MBq) in 3 mL microreactor vial and allowed to react for 15 min. 100 µL of this solution with or without reference standard (20 µg) were injected into a semiprep C-18 HPLC column equipped with a variable wavelength UV-Vis detector and a radiation detector (conditions C). The radioactive peaks were collected and the radioactivity of each fraction measured using a Capintec dose calibrator. The radiochemical yield was calculated as radioactivity in the peak corrected for decay over radioactivity injected.

Example 7

Radiochemical synthesis of [$^{18}$F]-3-fluoro-4-nitropyridine N-oxide ([$^{18}$F]-9) from 3-fluoro-4-nitropyridine N-oxide (9) by $^{19}$F/$^{18}$F exchange: 100 µL of 3-fluoro-4-nitropyridine N-oxide (9) dissolved in DMSO (1 mg/mL) was added to 100 µL of [$^{18}$F]-TBAF solution (~10 mCi, ~370 MBq) in 3 mL microreactor vial and allowed to react for 1 min. 100 µL of this solution were injected into a semiprep C-18 HPLC column equipped with a variable wavelength UV-Vis detector and a radiation detector (conditions E). The radioactive peaks were collected and the radioactivity of each fraction measured using a Capintec dose calibrator. The radiochemical yield was calculated as radioactivity in the peak corrected for decay over radioactivity injected.

Example 8

Synthesis of [$^{18}$F]-3-fluoro-4-aminopyridine ([$^{18}$F]-10): 1-10 mCi (37-370 MBq) of [$^{18}$F]-3-fluoro-4-aminopyridine N-oxide ([$^{18}$F]-9) containing 20-100 µg of cold 3-fluoro-4-aminopyridine N-oxide was dissolved in 4 mL of MeOH and the reaction was carried out as described above. The presence of cold compound facilitated obtaining reproducible yields. The product was purified by semiprep HPLC (conditions D). The final specific activity was 10-100 mCi/µmol (0.37-3.7 GBq/µmol).

Procurement of [$^{18}$F]-fluoride: Cyclotron-produced no-carrier-added aqueous $^{18}$F fluoride was obtained from IBA Molecular North America, Inc.

HPLC conditions (A-E): A. Nucleodur 5 µm, 4.6×250 mm C18ec (Macherey-Nagel). Flow 1.4 mL/min. Solvent A: 50 mM NH$_4$HCO$_3$, pH 8.0. Solvent B: 100% MeOH. Method: 0-2 min: 5% B, 2-6 min: 5-50% B, 6-12 min: 50% B, 12-12.5 min: 50-5% B, 12.5-17 min: 5% B. B. Nucleodur 5 µm, 4.6×250 mm C18ec (Macherey-Nagel). Flow 1.4 mL/min. Solvent A: 50 mM NH$_4$HCO$_3$, pH 8.0. Solvent B: 100% MeOH. Method: 0-2 min: 1% B, 2-9 min: 1-20% B, 9-11 min: 20% B, 11-11.5 min: 20-1% B, 11.5-14 min: 5% B. C. Eclipse XDB 5 µm, 9.4×250 mm C18 column (Agilent). Flow 4: mL/min. Mobile phase: 50 µM NaH$_4$PO$_4$, 10 mM triethylamine, pH 8.0, 5% EtOH. Isocratic: 0-20 min. D. Eclipse XDB 5 µm, 9.4×250 mm C18 column (Agilent). Flow: 4 mL/min. Solvent A: 50 mM NH$_4$HCO$_3$, pH 8.0. Solvent B: 100% MeOH. Method: 0-14 min: 5% B, 14-17 min: 5-25% B, 17-19 min: 25% B, 19-20 min: 25-5% B, 20-25 min: 5% B. E. Eclipse XDB 5 µm, 9.4×250 mm C18 column (Agilent). Flow 4: mL/min.

Mobile phase: 50 mM NaH$_4$PO$_4$, 10 mM triethylamine, pH 8.0, 5% EtOH. Isocratic: 0-10 min. RadioTLC analysis: The radioactive sample was spotted on a 25×75 mm TLC plate (PE SIL G, Whatman) next to the non-radioactive standard (1 mg/mL). The TLC was run in 95:5 methanol: acetic acid.

Reference NMR data of the used compounds.

3-bromo-4-nitropyridine (3): $^1$H-NMR (d$_6$-DMSO, 500 MHz) δ (ppm): 8.06 (1H, t, J =1.3 Hz), 8.85 (1H, d, J=1.3 Hz), 9.11 (1H, s). $^{13}$C-NMR (d$_6$-DMSO, 125 MHz) δ: (ppm) 102.0 (s), 122.6 (s), 137.1 (s), 139.3 (s), 142.7 (s).

3-iodo-4-nitropyridine (4): $^1$H-NMR (d$_6$-DMSO, 500 MHz) δ (ppm): 7.99 (1H, d, J=5.2 Hz), 8.80 (1H, d, J=5.2 Hz), 9.23 (1H, s). $^{13}$C-NMR (d$_6$-DMSO, 125 MHz) δ (ppm): 83.5 (s), 118.2 (s), 150.0 (s), 158.4 (s), 159.8 (s).

3-fluoro-4-nitropyridine (5): $^1$H-NMR (d$_6$-DMSO, 500 MHz) δ (ppm): 8.13 (1H, t, J =6.2 Hz), 8.75 (1H, d, J=5.25 Hz), 9.03 (1 H, d, J=2.9 Hz). $^{13}$C-NMR (d$_6$-DMSO, 125 MHz) δ (ppm): 118.4 (s), 118.5 (s), 141.9 (d, J=23.1), 149.7

(d, J=269.5). $^{19}$F-NMR (d$_6$-DMSO, 470 MHz) δ (ppm): −135.13 (dd, J$_2$=8.9 Hz, J$_1$=2.5 Hz).

3-bromo-4-fluoropyridine (6): $^1$H-NMR (d$_6$-DMSO, 500 MHz) δ (ppm): 7.50 (1H, dd, J$_2$=9.0 Hz, J$_1$=5.5 Hz), 8.56 (1H, dd, J$_2$=7.5 Hz, J$_1$=5.5 Hz), 8.81 (1 H, J: 9.5 Hz). $^{13}$C-NMR (d$_6$-DMSO, 125 MHz) δ (ppm): 106.0 (s), 112.9 (d, J: 16.2 Hz), 151.1 (d, J: 6.2 Hz), 153.5 (s), 165.0 (d, J: 275.4 Hz). $^{19}$F-NMR (d$_6$-DMSO, 470 MHz) δ (ppm): −99.14 (dd, J$_2$=16.9 Hz, J$_1$=9.1 Hz).

3-bromo-4-nitropyridine N-oxide (8): $^1$H-NMR (d$_6$-DMSO, 500 MHz) δ (ppm): 8.15 (1H, d, J=7.1 Hz), 8.38 (1H, dd, J$_2$=7.1 Hz, J$_1$=2.0 Hz), 8.85 (1 H, d, J=1.9 Hz). $^{13}$C-NMR (d$_6$-DMSO, 125 MHz) δ (ppm): 110.3 (s), 118.5 (s), 150.8 (s), 150.9 (s), 154.3 (s).

3-fluoro-4-nitropyridine N-oxide (9): $^1$H-NMR (d$_6$-DMSO, 500 MHz) δ (ppm): 8.24 (1H, dd, J$_2$=31.6 Hz, J$_1$=0.8 Hz), 8.25 (1H, dd, J$_2$=35.1 Hz, J$_1$=1.8 Hz), 8.91 (1 H, dd, J$_2$=7.1 Hz, J$_1$=1.8 Hz). $^{13}$C-NMR (d$_6$-DMSO, 125 MHz) δ (ppm): 122.3 (s), 131.4 (s), 131.7 (s), 137.0 (d, J=4.3), 153.3 (d, J=264.8). $^{19}$F-NMR (d$_6$-DMSO, 470 MHz) δ (ppm): −126.7 (dd, J$_2$=8.5 Hz, J$_1$=0.8 Hz).

3-bromopyridine (11): $^1$H-NMR (d$_6$-DMSO, 500 MHz) δ (ppm): 7.38 (1H, dd, J$_2$=8.1 Hz, J$_1$=3.5 Hz), 7.85 (1H, dt, J$_2$=8.2 Hz, J$_1$=1.0 Hz), 8.56 (1 H, m), 8.69 (1 H, d, J=2.3 Hz).

3-fluoropyridine (12): $^1$H-NMR (d$_6$-DMSO, 500 MHz) δ (ppm): 7.47 (1H, m), 7.70 (1H, dt, J$_2$=7.5 Hz, J$_1$=1.5 Hz), 8.44 (1 H, m), 8.56 (1 H, d, J=3.0 Hz). $^{19}$F-NMR (d$_6$-DMSO, 470 MHz) δ (ppm): −127.9 (t, J=5.1 Hz).

3-bromopyridine N-oxide (13): $^1$H-NMR (d$_6$-DMSO, 500 MHz) δ (ppm): 7.37 (1H, t, J=7.8 Hz), 7.58 (1H, d, J=7.6 Hz), 8.25 (1 H, d, J=7.1 Hz), 8.56 (1 H, s).

3-fluoropyridine N-oxide (14): $^1$H-NMR (d$_6$-DMSO, 500 MHz) δ (ppm): 7.40 (1H, dt, J$_2$=55.4 Hz, J$_1$=7.9 Hz), 7.42 (1H, dd, J$_2$=54.5 Hz, J$_1$=7.2 Hz), 8.13 (1 H, d, J=6.4 Hz), 8.51 (1 H, s). $^{19}$F-NMR (d$_6$-DMSO, 470 MHz) δ (ppm): −122.1 (td, J$_2$=5.3 Hz, J$_1$=0.8 Hz).

The claims are not to be interpreted as including means-plus- or step-plus-function limitations, unless such a limitation is explicitly recited in a given claim using the phrase(s) "means for" or "step for," respectively.

REFERENCES

1. S. Preshlock, M. Tredwell and V. Gouverneur, *Chemical Reviews*, 2016, 116, 719-766.
2. M. Karramkam, F. Hinnen, F. Vaufrey and F. Dollé, *Journal of Labelled Compounds and Radiopharmaceuticals*, 2003, 46, 979-.992.
3. J. H. Chun, C. L. Morse, F. T. Chin and V. W. Pike, *Chem Commun (Camb)*, 2013, 49, 2151-2153
4. H. F. Beer, M. Haeberli, S. Ametamey and P. A. Schubiger, *Journal of Labelled Compounds and Radiopharmaceuticals*, 1995, 36, 933-945.
5. A. Abrahim, P. Angelberger, K. Kletter, M. Müller, C. Joukhadar, T. Erker and O. Langer, *Journal of Labelled Compounds and Radiopharmaceuticals*, 2006, 49, 345-356.
6. H. Liu, S. Liu, Z. Miao, Z. Deng, B. Shen, X. Hong and Z. Cheng, *Journal of medicinal chemistry*, 2013, 56, 895-901.
7. M. A. Carroll, J. Nairne and J. L. Woodcraft, *Journal of Labelled Compounds and Radiopharmaceuticals*, 2007, 50, 452-454.
8. J. H. Chun and V. W. Pike, *Chem Commun (Camb)*, 2012, 48, 9921-9923.
9. B. H. Rotstein, N. A. Stephenson, N. Vasdev and S. H. Liang, *Nature communications*, 2014, 5, 4365.
10. P. Brugarolas, J. Sanchez-Rodriguez, A. V. Caprariello, J. Lacroix, C.-T. Chen, D. E. Appelbaum, R. H. Miller, F. Bezanilla and B. Popko, 2014.
11. P. Brugarolas, J. Sanchez-Rodriguez, J. Lacroix, F. Bezanilla, C.-T. Chen, D. Appelbaum and B. Popko, *J NUCL MED MEETING ABSTRACTS*, 2014, 55, 1124.
12. P. Brugarolas, J. Sanchez-Rodriguez, J. Lacroix, C.-T. Chen, F. Bezanilla and B. Popko, *Journal of Nuclear Medicine*, 2015, 56, 493.
13. M. Tredwell and V. Gouverneur, *Angew Chem Int Ed Engl*, 2012, 51, 11426-11437.
14. R. M. Johnson, *Journal of the Chemical Society B: Physical Organic*, 1966, DOI: 10.1039/J29660001058, 1058-1061.
15. E. Blom, F. Karimi and B. Långström, *Journal of Labelled Compounds and Radiopharmaceuticals*, 2009, 52, 504-511.
16. Z. Liu, M. Pourghiasian, F. Benard, J. Pan, K. S. Lin and D. M. Perrin, *Journal of nuclear medicine: official publication, Society of Nuclear Medicine*, 2014, 55, 1499-1505.
17. Z. Liu, G. Amouroux, Z. Zhang, J. Pan, N. Hundal-Jabal, N. Colpo, J. Lau, D. M. Perrin, F. Benard and K. S. Lin, *Mol Pharm*, 2015, 12, 974-982.

The invention claimed is:

1. A method for synthesizing a fluorinated aromatic N-heterocyclic N-oxide compound, said method comprising reacting an aromatic N-heterocyclic N-oxide compound with a fluoride source; wherein the aromatic N-heterocyclic N-oxide compound comprises a leaving group.

2. The method of claim 1, wherein the leaving group is a halide, nitro, protonated ammonium, protonated alkylammonium, trialkylammonium, mesylate, tosylate, phenoxide, carboxylate, thiolate, or diazonium.

3. The method of claim 1, wherein the fluoride source is a nucleophilic fluoride source.

4. The method of claim 2, wherein the nucleophilic fluoride source is selected from the group consisting of tetrabutylammonium fluoride (TBAF), tetramethylammonium fluoride (TMAF), (diethylamino)sulfur trifluoride (DAST), bis(2-methoxyethyl)aminosulfur trifluoride (deoxofluor), 4-morpholinosulfur trifluoride (MOST), CsF, NaF, and KF.

5. The method of claim 1, wherein the aromatic N-heterocyclic N-oxide compound comprises a leaving group that is ortho-, meta-, or para- to the N-oxide.

6. The method of claim 1, wherein the reducing composition comprises hydrogen and a transition metal absorbed onto a solid support, a boron reagent, an aluminum reagent, a tin reagent, or a silane.

7. The method of claim 6, wherein the transition metal is palladium, platinum, nickel, or rhodium.

8. The method of claim 6, wherein the solid support is carbon, alumina, calcium carbonate, or silica.

9. The method of claim 6, wherein the boron reagent is sodium borohydride, sodium cyanoborohydride, zinc borohydrode, a tetraorganylammonium tetrahydroborate, lithium triethylborohydride, lithium tri-sec-butyl borohydride, L-selectride, sodium triacetoxyborohydride, or sulfurated sodium borohydride.

10. The method of claim 6, wherein the aluminum reagent is aluminum hydride, lithium aluminum hydride, lithium tri-tert-butoxy aluminum hydride, DIBAL-H, or sodium bis(2-methoxyethoxy)aluminumhydride.

11. The method of claim 6, wherein the tin reagent is tributyltin hydride.

12. The method of claim 6, wherein the silane reagent is an alkylsilane, an alkylsiloxane, a phenylsilane, or a halosilane.

13. The method of claim 1, wherein the aromatic N-heterocyclic N-oxide compound comprising a leaving group is substituted or unsubstituted.

14. A method for synthesizing a fluorinated aromatic N-heterocyclic compound, said method comprising
   reacting an aromatic N-oxide compound with a fluoride source, wherein the aromatic N-oxide compound comprises a leaving group;
   and reducing the N-oxide group with a reducing composition to give a fluorinated aromatic N-heterocyclic compound.

15. The method of claim 14, wherein the leaving group is a halide, nitro, protonated ammonium, protonated alkylammonium, trialkylammonium, mesylate, tosylate, phenoxide, carboxylate, thiolate, or diazonium.

16. The method of claim 14, wherein the fluoride source is a nucleophilic fluoride source.

17. The method of claim 16, wherein the nucleophilic fluoride source is selected from the group consisting of tetrabutylammonium fluoride (TBAF), tetramethylammonium fluoride (TMAF), (diethylamino)sulfur trifluoride (DAST), bis(2-methoxyethyl)aminosulfur trifluoride (deoxofluor), 4-morpholinosulfur trifluoride (MOST), CsF, NaF, KF, and KF-kryptofix.

18. The method of claim 14, wherein the aromatic N-oxide compound comprises a leaving group that is ortho-, meta-, or para- to the N-oxide.

\* \* \* \* \*

UNITED STATES PATENT AND TRADEMARK OFFICE
CERTIFICATE OF CORRECTION

| | | |
|---|---|---|
| PATENT NO. | : 10,160,695 B2 | Page 1 of 1 |
| APPLICATION NO. | : 15/497747 | |
| DATED | : December 25, 2018 | |
| INVENTOR(S) | : Brugarolas | |

It is certified that error appears in the above-identified patent and that said Letters Patent is hereby corrected as shown below:

In the Specification

In Column 1, at Line 12, insert the following subtitle and paragraph:
-- GOVERNMENT SUPPORT CLAUSE
This invention was made with government support under grant numbers EB020075, NS084382 awarded by the National Institutes of Health. The government has certain rights in the invention. --

Signed and Sealed this
Twelfth Day of September, 2023

Katherine Kelly Vidal
*Director of the United States Patent and Trademark Office*